(12) United States Patent  
Hayter et al.

(10) Patent No.: US 10,888,272 B2  
(45) Date of Patent: Jan. 12, 2021

(54) SYSTEMS, DEVICES, AND METHODS FOR MEAL INFORMATION COLLECTION, MEAL ASSESSMENT, AND ANALYTE DATA CORRELATION

(71) Applicant: ABBOTT DIABETES CARE INC., Alameda, CA (US)

(72) Inventors: Gary A. Hayter, Oakland, CA (US); Timothy C. Dunn, San Francisco, CA (US); Nathan Crouther, San Francisco, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 696 days.

(21) Appl. No.: 15/206,095

(22) Filed: Jul. 8, 2016

(65) Prior Publication Data

US 2017/0128007 A1     May 11, 2017

Related U.S. Application Data

(60) Provisional application No. 62/307,346, filed on Mar. 11, 2016, provisional application No. 62/307,344, (Continued)

(51) Int. Cl.
*G09G 5/02*     (2006.01)  
*A61B 5/00*     (2006.01)  
(Continued)

(52) U.S. Cl.  
CPC .......... *A61B 5/4866* (2013.01); *A61B 5/0002* (2013.01); *A61B 5/1495* (2013.01); *A61B 5/14532* (2013.01); *A61B 5/14542* (2013.01); *A61B 5/14546* (2013.01); *A61B 5/14865* (2013.01); *A61B 5/486* (2013.01); *A61B 5/4839* (2013.01); *A61B 5/6849* (2013.01); *A61B 5/6898* (2013.01); *A61B 5/7246* (2013.01);  
(Continued)

(58) Field of Classification Search  
CPC ...................................................... A61B 5/486  
See application file for complete search history.

(56) References Cited

U.S. PATENT DOCUMENTS 4,545,382 A    10/1985   Higgins et al.  
4,711,245 A    12/1987   Higgins et al.  
(Continued)

FOREIGN PATENT DOCUMENTS

WO    WO 2015/153482 A1    10/2015

*Primary Examiner* — Robert A Sorey  
*Assistant Examiner* — Kristine K Rapillo  
(74) *Attorney, Agent, or Firm* — One LLP

(57) ABSTRACT

Systems, devices, and methods for detecting, measuring and classifying meals for an individual based on analyte measurements. These results and related information can be presented to the individual to show the individual which meals are causing the most severe analyte response. These results can be organized and categorized based on preselected criteria or previous meals and results so as to organize and present the results in a format with reference to glucose as the monitored analyte. Various embodiments disclosed herein relate to methods, systems, and software applications intended to engage an individual by providing direct and timely feedback regarding the individual's meal-related glycemic response.

20 Claims, 15 Drawing Sheets

Related U.S. Application Data filed on Mar. 11, 2016, provisional application No. 62/191,218, filed on Jul. 10, 2015, provisional application No. 62/191,262, filed on Jul. 10, 2015.

(51) Int. Cl.
  *G09B 19/00*    (2006.01)
  *G09B 5/02*     (2006.01)
  *A61B 5/145*    (2006.01)
  *A61B 5/1486*   (2006.01)
  *A61B 5/1495*   (2006.01)

(52) U.S. Cl.
  CPC .......... *A61B 5/7282* (2013.01); *A61B 5/742* (2013.01); *A61B 5/7475* (2013.01); *G09B 5/02* (2013.01); *G09B 19/0092* (2013.01)

(56) References Cited

U.S. PATENT DOCUMENTS

| | | |
|---|---|---|
| 5,262,035 A | 11/1993 | Gregg et al. |
| 5,262,305 A | 11/1993 | Heller et al. |
| 5,264,104 A | 11/1993 | Gregg et al. |
| 5,320,715 A | 6/1994 | Berg |
| 5,356,786 A | 10/1994 | Heller et al. |
| 5,509,410 A | 4/1996 | Hill et al. |
| 5,543,326 A | 8/1996 | Heller et al. |
| 5,593,852 A | 1/1997 | Heller et al. |
| 5,601,435 A | 2/1997 | Quy |
| 5,628,890 A | 5/1997 | Carter et al. |
| 5,820,551 A | 10/1998 | Hill et al. |
| 5,822,715 A | 10/1998 | Worthington et al. |
| 5,899,855 A | 5/1999 | Brown |
| 5,918,603 A | 7/1999 | Brown |
| 6,071,391 A | 6/2000 | Gotoh et al. |
| 6,103,033 A | 8/2000 | Say et al. |
| 6,120,676 A | 9/2000 | Heller et al. |
| 6,121,009 A | 9/2000 | Heller et al. |
| 6,134,461 A | 10/2000 | Say et al. |
| 6,143,164 A | 11/2000 | Hsieh et al. |
| 6,144,837 A | 11/2000 | Quy |
| 6,161,095 A | 12/2000 | Brown |
| 6,175,752 B1 | 1/2001 | Say et al. |
| 6,270,455 B1 | 8/2001 | Brown |
| 6,284,478 B1 | 9/2001 | Heller et al. |
| 6,299,757 B1 | 10/2001 | Feldman et al. |
| 6,338,790 B1 | 1/2002 | Feldman et al. |
| 6,377,894 B1 | 4/2002 | Deweese et al. |
| 6,461,496 B1 | 10/2002 | Feldman et al. |
| 6,503,381 B1 | 1/2003 | Gotoh et al. |
| 6,514,460 B1 | 2/2003 | Fendrock |
| 6,514,718 B2 | 2/2003 | Heller et al. |
| 6,540,891 B1 | 4/2003 | Stewart et al. |
| 6,560,471 B1 | 5/2003 | Heller et al. |
| 6,579,690 B1 | 6/2003 | Bonnecaze et al. |
| 6,591,125 B1 | 7/2003 | Buse et al. |
| 6,592,745 B1 | 7/2003 | Feldman et al. |
| 6,600,997 B2 | 7/2003 | Deweese et al. |
| 6,605,200 B1 | 8/2003 | Mao et al. |
| 6,605,201 B1 | 8/2003 | Mao et al. |
| 6,616,819 B1 | 9/2003 | Liamos et al. |
| 6,618,934 B1 | 9/2003 | Feldman et al. |
| 6,650,471 B2 | 11/2003 | Doi |
| 6,654,625 B1 | 11/2003 | Say et al. |
| 6,676,816 B2 | 1/2004 | Mao et al. |
| 6,730,200 B1 | 5/2004 | Stewart et al. |
| 6,736,957 B1 | 5/2004 | Forrow et al. |
| 6,746,582 B2 | 6/2004 | Heller et al. |
| 6,749,740 B2 | 6/2004 | Liamos et al. |
| 6,764,581 B1 | 7/2004 | Forrow et al. |
| 6,773,671 B1 | 8/2004 | Lewis et al. |
| 6,881,551 B2 | 4/2005 | Heller et al. |
| 6,893,545 B2 | 5/2005 | Gotoh et al. |
| 6,932,892 B2 | 8/2005 | Chen et al. |
| 6,932,894 B2 | 8/2005 | Mao et al. |
| 6,942,518 B2 | 9/2005 | Liamos et al. |
| 7,041,468 B2 | 5/2006 | Drucker et al. |
| 7,167,818 B2 | 1/2007 | Brown |
| 7,299,082 B2 | 11/2007 | Feldman et al. |
| 7,501,053 B2 | 3/2009 | Karinka et al. |
| 7,618,369 B2 | 11/2009 | Hayter et al. |
| 7,740,581 B2 | 6/2010 | Buse et al. |
| 7,754,093 B2 | 7/2010 | Forrow et al. |
| 7,802,467 B2 | 9/2010 | Wang |
| 7,811,231 B2 | 10/2010 | Jin et al. |
| 7,811,430 B2 | 10/2010 | Petyt et al. |
| 7,822,557 B2 | 10/2010 | Chen et al. |
| 7,846,311 B2 | 12/2010 | Feldman et al. |
| 7,866,026 B1 | 1/2011 | Wang et al. |
| 7,885,698 B2 | 2/2011 | Feldman |
| 7,887,682 B2 | 2/2011 | Wang et al. |
| 7,895,740 B2 | 3/2011 | Wang et al. |
| 7,918,975 B2 | 4/2011 | Wang et al. |
| 8,219,173 B2 | 7/2012 | Budiman et al. |
| 8,298,389 B2 | 10/2012 | Chen et al. |
| 8,346,335 B2 | 1/2013 | Harper et al. |
| 8,595,607 B2 | 11/2013 | Nekoomaram et al. |
| 8,771,183 B2 | 7/2014 | Sloan |
| 9,171,343 B1 * | 10/2015 | Fischell ............ A61M 5/1723 |
| 9,402,544 B2 | 8/2016 | Yee et al. |
| 9,465,917 B2 * | 10/2016 | Soni .......... G16H 50/30 |
| 2003/0208113 A1 * | 11/2003 | Mault ............ A61B 5/415 |
| | | 600/316 |
| 2006/0091006 A1 | 5/2006 | Wang et al. |
| 2007/0095661 A1 | 5/2007 | Wang et al. |
| 2007/0233013 A1 | 10/2007 | Schoenberg |
| 2008/0161666 A1 | 7/2008 | Feldman et al. |
| 2008/0267823 A1 | 10/2008 | Wang et al. |
| 2009/0294277 A1 | 12/2009 | Thomas et al. |
| 2010/0081905 A1 | 4/2010 | Bommakanti et al. |
| 2010/0198034 A1 | 8/2010 | Thomas et al. |
| 2010/0213057 A1 | 8/2010 | Feldman et al. |
| 2010/0230285 A1 | 9/2010 | Hoss et al. |
| 2010/0326842 A1 | 12/2010 | Mazza et al. |
| 2011/0021889 A1 | 1/2011 | Hoss et al. |
| 2011/0213225 A1 | 9/2011 | Bernstein et al. |
| 2012/0150005 A1 | 6/2012 | Hoss et al. |
| 2012/0227737 A1 * | 9/2012 | Mastrototaro ...... G06F 19/3456 |
| | | 128/203.14 |
| 2013/0085358 A1 | 4/2013 | Crouther et al. |
| 2014/0350369 A1 | 11/2014 | Budiman et al. |
| 2015/0119655 A1 * | 4/2015 | Mayou ............ A61B 5/7282 |
| | | 600/301 |
| 2015/0205947 A1 | 7/2015 | Berman et al. |
| 2015/0341438 A1 | 11/2015 | Sloan et al. |

\* cited by examiner

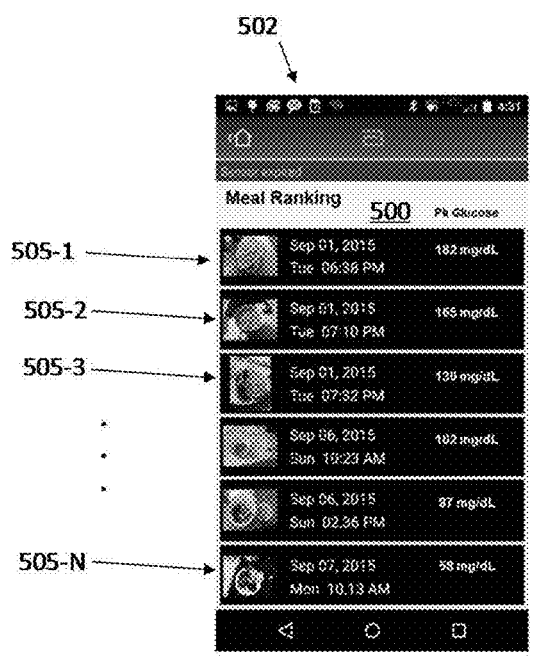
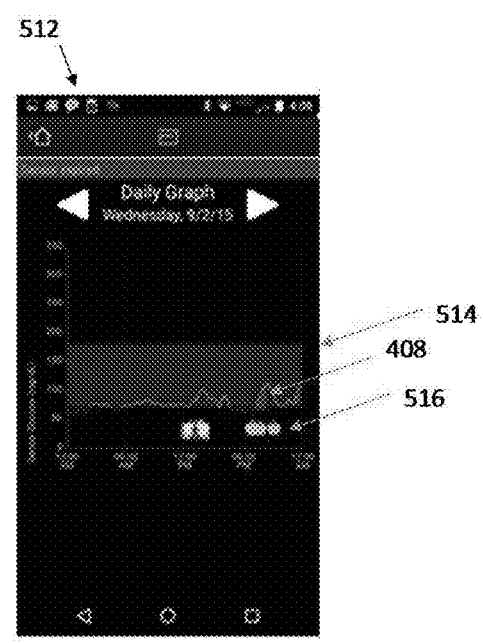
FIG. 5A                    FIG. 5B

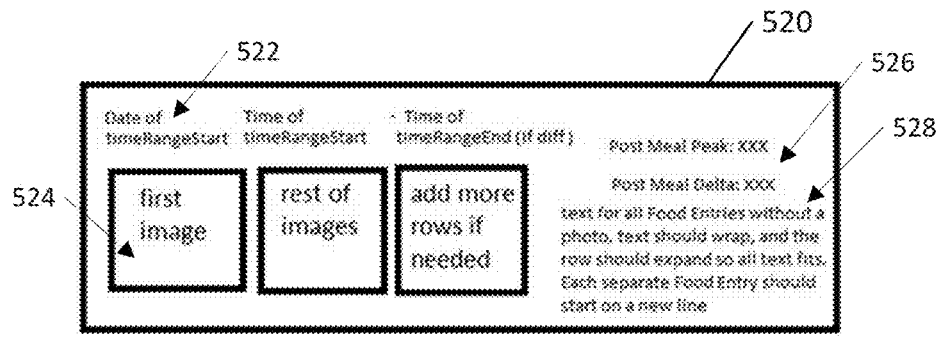
FIG. 5C
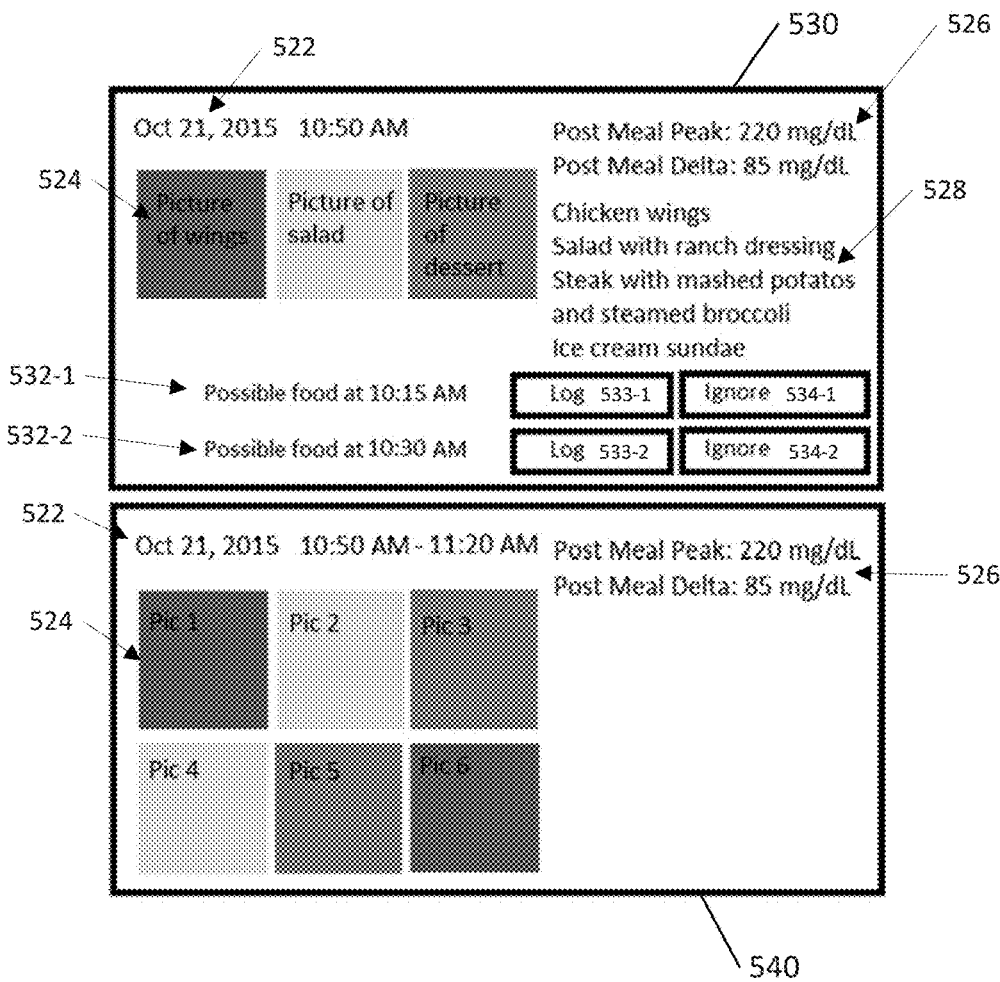
FIG. 5D
FIG. 5E

SYSTEMS, DEVICES, AND METHODS FOR MEAL INFORMATION COLLECTION, MEAL ASSESSMENT, AND ANALYTE DATA CORRELATION

CROSS-REFERENCE TO RELATED APPLICATIONS

This application claims priority to, and the benefit of, U.S. Provisional Application No. 62/191,218, filed Jul. 10, 2015, U.S. Provisional Application No. 62/191,262, filed Jul. 10, 2015, U.S. Provisional Application No. 62/307,344, filed Mar. 11, 2016, and U.S. Provisional Application No. 62/307,346, filed Mar. 11, 2016, all of which are incorporated by reference herein in their entireties for all purposes.

FIELD

The present subject matter broadly relates to systems, devices, and methods for the collection of information about analyte levels of certain individuals and information about meals that those individuals consume. The present subject matter further relates to processing, analyzing, and/or presenting this information for the purpose of correlating meal information to analyte levels, and identifying and implementing adjustments to the diet, lifestyle, and/or medical treatment regimens of those individuals.

BACKGROUND

The increased prevalence of Type 2 diabetes and Metabolic Syndrome over the past few decades has been attributed to changing diet and activity levels. For example, consumption of more readily available high glycemic index (GI) foods cause rapid post-prandial increase of blood glucose and insulin levels, which has a positive association with weight gain and obesity. These conditions can be further traced to an increased risk of developing these and other diseases.

Most people generally understand the importance of their diet. However, in practice, many people struggle with translating this general awareness to their specific food choices. These problems exist primarily because people cannot directly see the impact of their food choices. This can lead to misconceptions around food portion size, and understanding of which foods are relatively healthy, and the necessary duration and intensity of activity to maintain good health. These misconceptions can be exacerbated by advertisements, habits, peer pressure, food preferences, and recommendations based on generalizations.

High glucose levels are primarily driven by the consumption of food. The level of post-prandial glucose is related to the amount of carbohydrates and other meal components consumed by the individual, as well as to the individual's physiological response to meals. Each individual's glycemic response can now be tracked and better understood by in vivo analyte (e.g., glucose) monitoring devices. However, a challenge for analysis of this influx of data is to represent the data in a meaningful manner that enables efficient action.

Understanding of the data related to meal selection, and subsequent results, needs to be made both on a clinical basis, as well as a personal basis for both the individual, meal administrator, and/or medical professional to understand and moderate glucose excursions, such as episodes of hyperglycemia.

Prior attempts to implement software for tracking the user's meal consumption and correlating that to the user's analyte data suffer from numerous deficiencies. For example, those prior systems that require the performance of what can be inconvenient and uncomfortable discrete blood glucose measurements, for example, by requiring an individual to perform a finger stick to place a blood sample on a test strip, suffer from a lack of a sufficient number of data points to adequately determine a glycemic response to the meal. For example, the individual may perform the discrete blood glucose measurement at a time before or after the time when the user's glycemic response peaks, making it difficult to accurately characterize the glycemic response and to compare meals based on the glycemic response. Also, this deficiency in data points makes it extremely difficult to automatically detect the occurrence of a meal event in the user's analyte data. Thus such systems place significant reliance upon manual logging of meals by the user.

Prior art systems that seek to detect meal events based simply on the existence of a rise in glucose levels, such as US 2003/0208113, are inadequate because they fail to take into account the user's prior meal history and thus can overestimate the number of meals the user has consumed.

Thus, improved systems, devices, and methods for meal information collection, meal assessment and detection, and correlation to analyte levels are needed.

SUMMARY

Provided herein are example embodiments of systems, devices, and methods for detecting, measuring, and classifying meals for a human individual in relation to that individual's analyte measurements. These individuals can be those exhibiting or diagnosed with a diabetic condition, those considered as pre-diabetic, those with metabolic syndrome, and even those without diabetes, pre-diabetic, or metabolic syndrome conditions. These individuals can be any person motivated to improve his or her health by adjustment to his or her diet and/or activity practices. Resulting information can be presented to the individual to show which meals or aspects of the meals are causing the most impact on analyte levels. These results can be organized and categorized based on preselected criteria chosen directly by the individual or based upon consultation between the individual and a medical professional.

In many embodiments, the individual's meal-related analyte responses collected by an analyte monitoring system, such as an in vivo analyte monitoring system, can be compared with or linked to meal information to discover common consistencies (or inconsistencies) along with trends therein based on related historical glucose readings and associated algorithms, variables, weights, comparisons, and trends.

Many embodiments disclosed herein are intended to engage the individual by providing direct and timely feedback regarding the individual's meal-related analyte response. In some embodiments, this analyte response can be provided to the individual to characterize the effects of meal consumption.

The present embodiments can be immediately informative and fun to use by the individual, thereby encouraging the individual's experimentation therewith to better understand how their own diet impacts their body's analyte response. The individual can compare and contrast their current and historical analyte data to see their how their own efforts are related to better diet and meal section and how these choices directly affect their health.

Example embodiments are also provided that enable the collection of analyte data from a local population and linking or association of that data with meal information about meals consumed by the local population. The aggregated information can be processed and presented to a user to identify common trends in analyte levels amongst the local population and to identify whether any correlation exists to the common diet of that population. For example, a person with responsibility for dietary selections can utilize the presented information to determine whether meal contents, types, and/or times of administration can or should be adjusted to alleviate an undesirable trend in the aggregate analyte data, such as a reduction in the occurrence of hypoglycemic or hyperglycemic events. These example embodiments have particular suitability for populations in a common living arrangement, examples of which can include senior care facilities, hospitals, rehabilitation centers, schools, dormitories, military compounds or bases, family residences, prison or penal populations, and any other such environment where a group of individuals share one or more meals on a regular basis.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be depicted schematically rather than literally or precisely.

FIGS. 4A-E and 5A-F depict example embodiments of graphical user interface display screens.

DETAILED DESCRIPTION

Figure 1:
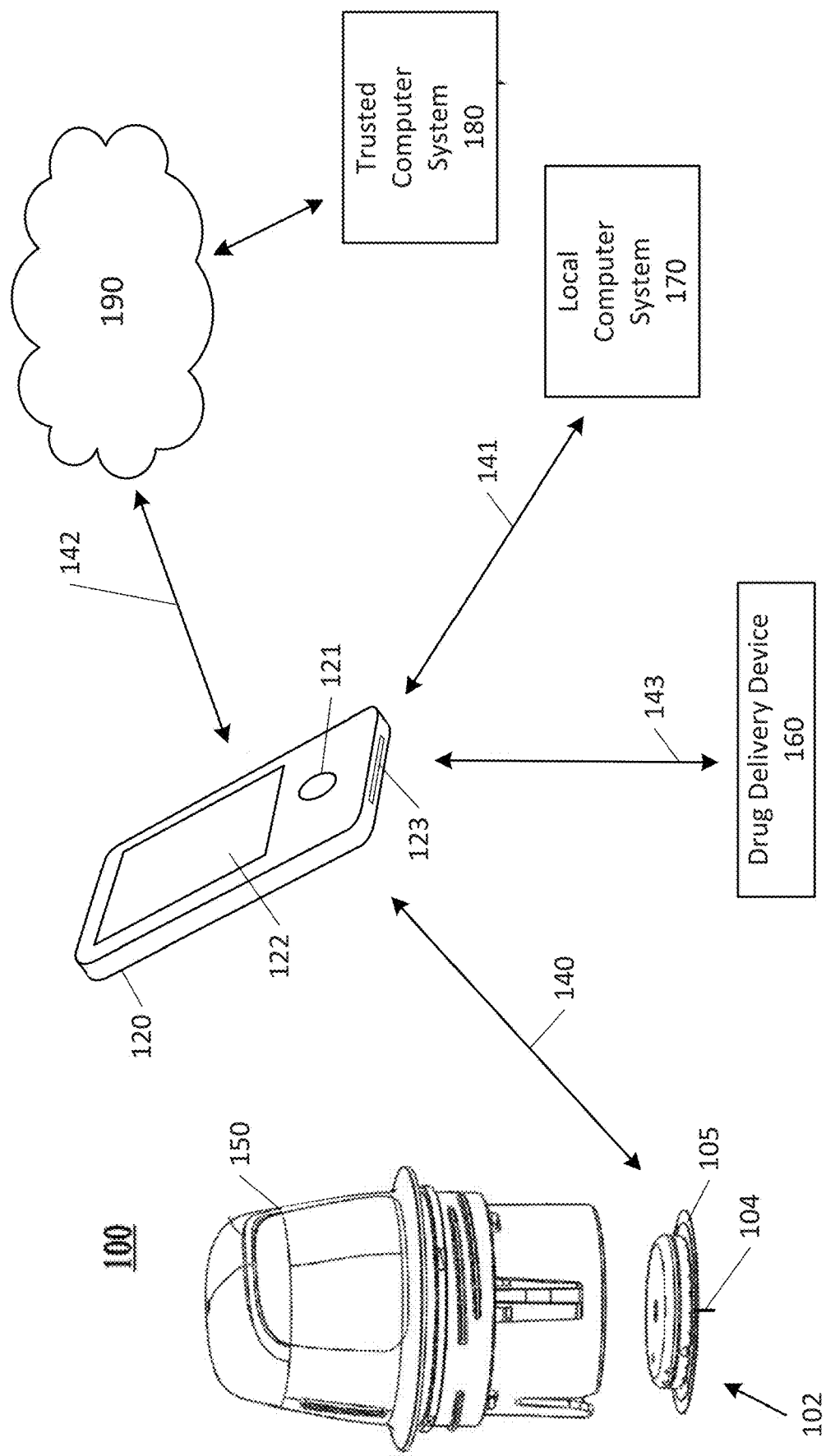
FIG. 1 is a high level diagram depicting an example embodiment of an analyte monitoring system for real time analyte (e.g., glucose) measurement, data acquisition and/or processing.

Provided herein are example embodiments of systems, devices, and methods for detecting, measuring, and classifying meals for a human individual in relation to that individual's analyte levels. Based on the analyte data collected, meal-related events and their impact on the individual's analyte levels can be further understood and used to modify future meal selection and dietary habits. Moreover, the administration schedule for insulin or other medication can be adjusted based upon the analyte response to particular meals.

Before describing this subject matter in greater detail, it is worthwhile to describe example embodiments of systems, devices, and methods with which the subject matter can be implemented.

A number of systems have been developed for the automatic monitoring of the analyte(s), like glucose, in bodily fluid such as in the blood stream, in interstitial fluid ("ISF"), dermal fluid of the dermal layer, or in other biological fluid. Some of these systems are configured so that at least a portion of a sensor is positioned below a skin surface of a user, e.g., in a blood vessel or in the subcutaneous tissue of a user, to obtain information about at least one analyte of the body.

As such, these systems can be referred to as "in vivo" monitoring systems. In vivo analyte monitoring systems include "Continuous Analyte Monitoring" systems (or "Continuous Glucose Monitoring" systems) that can broadcast data from a sensor control device to a reader device continuously without prompting, e.g., automatically according to a broadcast schedule. In vivo analyte monitoring systems also include "Flash Analyte Monitoring" systems (or "Flash Glucose Monitoring" systems or simply "Flash" systems) that can transfer data from a sensor control device in response to a scan or request for data by a reader device, such as with an Near Field Communication (NFC) or Radio Frequency Identification (RFID) protocol. In vivo analyte monitoring systems can also operate without the need for finger stick calibration.

The in vivo analyte monitoring systems can be differentiated from "in vitro" systems that contact a biological sample outside of the body (or rather "ex vivo") and that typically include a meter device that has a port for receiving an analyte test strip carrying bodily fluid of the user, which can be analyzed to determine the user's blood sugar level. While in many of the present embodiments the monitoring is accomplished in vivo, the embodiments disclosed herein can be used with in vivo analyte monitoring systems that incorporate in vitro capability, as well has purely in vitro or ex vivo analyte monitoring systems.

The sensor can be part of the sensor control device that resides on the body of the user and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few.

In vivo monitoring systems can also include a device that receives sensed analyte data from the sensor control device and processes and/or displays that sensed analyte data, in any number of forms, to the user. This device, and variations thereof, can be referred to as a "reader device" (or simply a "reader"), "handheld electronics" (or a handheld), a "portable data processing" device or unit, a "data receiver," a "receiver" device or unit (or simply a receiver), or a "remote" device or unit, to name a few. Other devices such as personal computers have also been utilized with or incorporated into in vivo and in vitro monitoring systems.

Embodiments of In Vivo Monitoring Systems

For purpose of illustration, and not limitation, the graphical user interfaces and associated software described herein may be used in connection with an exemplary analyte monitoring system as depicted in FIG. 1. FIG. 1 is an illustrative view depicting an example in vivo analyte monitoring system 100 with which any and/or all of the embodiments described herein can be used. System 100 can have a sensor control device 102 and a reader device 120 that communicate with each other over a local communication path (or link) 140, which can be wired or wireless, and uni-directional or bi-directional. In embodiments where local communication path 140 is wireless, any near field communication (NFC) protocol, RFID protocol, Bluetooth or Bluetooth Low Energy protocol, Wi-Fi protocol, proprietary protocol, or the like can be used, including those communication protocols in existence as of the date of this filing or their later developed variants.

Bluetooth is a well-known standardized short range wireless communication protocol, and Bluetooth Low Energy is a version of the same that requires less power to operate. Bluetooth Low Energy (Bluetooth LE, BTLE, BLE) is also referred to as Bluetooth Smart or Bluetooth Smart Ready. A version of BTLE is described in the Bluetooth Specification, version 4.0, published Jun. 30, 2010, which is explicitly incorporated by reference herein for all purposes. The term "NFC" applies to a number of protocols (or standards) that set forth operating parameters, modulation schemes, coding, transfer speeds, frame format, and command definitions for NFC devices. The following is a non-exhaustive list of examples of these protocols, each of which (along with all of its sub-parts) is incorporated by reference herein in its entirety for all purposes: ECMA-340, ECMA-352, ISO/IEC 14443, ISO/IEC 15693, ISO/IEC 16000-3, ISO/IEC 18092, and ISO/IEC 21481.

Reader device 120 is also capable of wired, wireless, or combined communication, either bidirectional or unidirectional, with either or all of: an drug delivery device 160 over communication path (or link) 143, a local computer system 170 over communication path (or link) 141, and with a network 190 over communication path (or link) 142. The same wireless protocols described for link 140 can likewise be used for all or part of links 141, 142, and 143.

Reader device 120 can communicate with any number of entities through network 190, which can be part of a telecommunications network, such as a Wi-Fi network, a local area network (LAN), a wide area network (WAN), the internet, or other data network for uni-directional or bi-directional communication. A trusted computer system 180 can be accessed through network 190. In an alternative embodiment, communication paths 141 and 142 can be the same path which can include the network 190 and/or additional networks. All communications over paths 140, 141, 142, and 143 can be encrypted and sensor control device 102, reader device 120, drug delivery device 160, remote computer system 170, and trusted computer system 180 can each be configured to encrypt and decrypt those communications sent and received.

Variants of devices 102 and 120, as well as other components of an in vivo-based analyte monitoring system that are suitable for use with the system, device, and method embodiments set forth herein, are described in US Patent Application Publ. No. 2011/0213225 (the '225 Publication), which is incorporated by reference herein in its entirety for all purposes.

Sensor control device 102 can include a housing 103 containing in vivo analyte monitoring circuitry and a power source (not shown). The in vivo analyte monitoring circuitry can be electrically coupled with an analyte sensor 104 that can extend through an adhesive patch 105 and project away from housing 103. Adhesive patch 105 contains an adhesive layer (not shown) for attachment to a skin surface of the body of the user. Other forms of body attachment to the body may be used, in addition to or instead of adhesive.

Sensor 104 is adapted to be at least partially inserted into the body of the user, where it can make fluid contact with that user's body fluid (e.g., interstitial fluid (ISF), dermal fluid, or blood) and be used, along with the in vivo analyte monitoring circuitry, to measure analyte-related data of the user. Generally, sensor control device 102 and its components can be applied to the body with a mechanical applicator 150 in one or more steps, as described in the incorporated '225 Publication, or in any other desired manner.

After activation, sensor control device 102 can wirelessly communicate the collected analyte data (such as, for example, data corresponding to monitored analyte level and/or monitored temperature data, and/or stored historical analyte related data) to reader device 120 where, in certain embodiments, it can be algorithmically processed into data representative of the analyte level of the user and then displayed to the user and/or otherwise incorporated into a diabetes monitoring regime.

Various embodiments disclosed herein relate to reader device 120, which can have a user interface including one or more of a display 122, keyboard, optional user interface component 121, and the like. Here, display 122 can output information to the user and/or accept an input from the user (e.g., if configured as a touch screen). Reader device 120 can include one or more optional user interface components 121, such as a button, actuator, touch sensitive switch, capacitive switch, pressure sensitive switch, jog wheel or the like. Reader device 120 can also include one or more data communication ports 123 for wired data communication with external devices such as local computer system 170. Reader device 120 may also include an integrated or attachable in vitro meter, including an in vitro test strip port (not shown) to receive an in vitro analyte test strip for performing in vitro blood analyte measurements.

Drug delivery device 160 is capable of injecting or infusing a drug, such as but not limited to insulin, into the body of the individual wearing sensor control device 102. Like reader device 120, the drug delivery device can include processing circuitry, non-transitory memory containing instructions executable by the processing circuitry, wireless or wired communication circuitry, and a user interface including one or more of a display, touchscreen, keyboard, an input button or instrument, and the like. Drug delivery device 160 can include a drug reservoir, a pump, an infusion tube, and an infusion cannula configured for at least partial implantation into the user's body. The pump can deliver insulin from the reservoir, through the tube, and then through the cannula into the user's body. Drug delivery device 160 can include instructions, executable by the processor, to control the pump and the amount of insulin delivered. These instructions can also cause calculation of insulin delivery amounts and durations (e.g., a bolus infusion and/or a basal infusion profile) based on analyte level measurements obtained directly or indirectly from sensor control device 102. Alternatively, calculations of insulin delivery amounts and durations, and the control of the pump, can be performed by reader device 120 directly. The drug delivery device can be configured to communicate directly with reader device 120 in the form of a closed loop or semi-closed loop system. Alternatively, the drug delivery device can include the functionality of reader device 120 described herein, or vice versa, to arrive at one integrated reader and drug delivery device.

Computer system 170 may be a personal or laptop computer, a tablet, or other suitable data processing device. Computer 170 can be either local (e.g., accessible via a direct wired connection such as USB) or remote to reader device 120 and can be (or include) software for data management and analysis and communication with the components in analyte monitoring system 100. Operation and use of computer 170 is further described in the '225 Publication incorporated herein by reference. Analyte monitoring system 100 can also be configured to operate with a data processing module (not shown), also as described in the incorporated '225 Publication.

Trusted computer system 180 can be used to perform authentication of sensor control device 102 and/or reader device 120, used to store confidential data received from devices 102 and/or 120, used to output confidential data to devices 102 and/or 120, or otherwise configured. Trusted computer system 180 can include one or more computers, servers, networks, databases, and the like. Trusted computer system 180 can be within the possession of the manufacturer or distributor of sensor control device 102, either physically or virtually through a secured connection, or can be maintained and operated by a different party (e.g., a third party).

Trusted computer system 180 can be trusted in the sense that system 100 can assume that computer system 180 provides authentic data or information. Trusted computer system 180 can be trusted simply by virtue of it being within the possession or control of the manufacturer, e.g., like a typical web server. Alternatively, trusted computer system 180 can be implemented in a more secure fashion such as by requiring additional password, encryption, firewall, or other internet access security enhancements that further guard against counterfeiter attacks or attacks by computer hackers.

The processing of data and the execution of software within system 100 can be performed by one or more processors of reader device 120, computer system 170, and/or sensor control device 102. For example, raw data measured by sensor 104 can be algorithmically processed into a value that represents the analyte level and that is readily suitable for display to the user, and this can occur in sensor control device 102, reader device 120, or computer system 170. This and any other information derived from the raw data can be displayed in any of the manners described above (with respect to display 122) on any display residing on any of sensor control device 102, reader device 120, or computer system 170. The information may be utilized by the user to determine any necessary corrective actions to ensure the analyte level remains within an acceptable and/or clinically safe range.

Figure 2A:
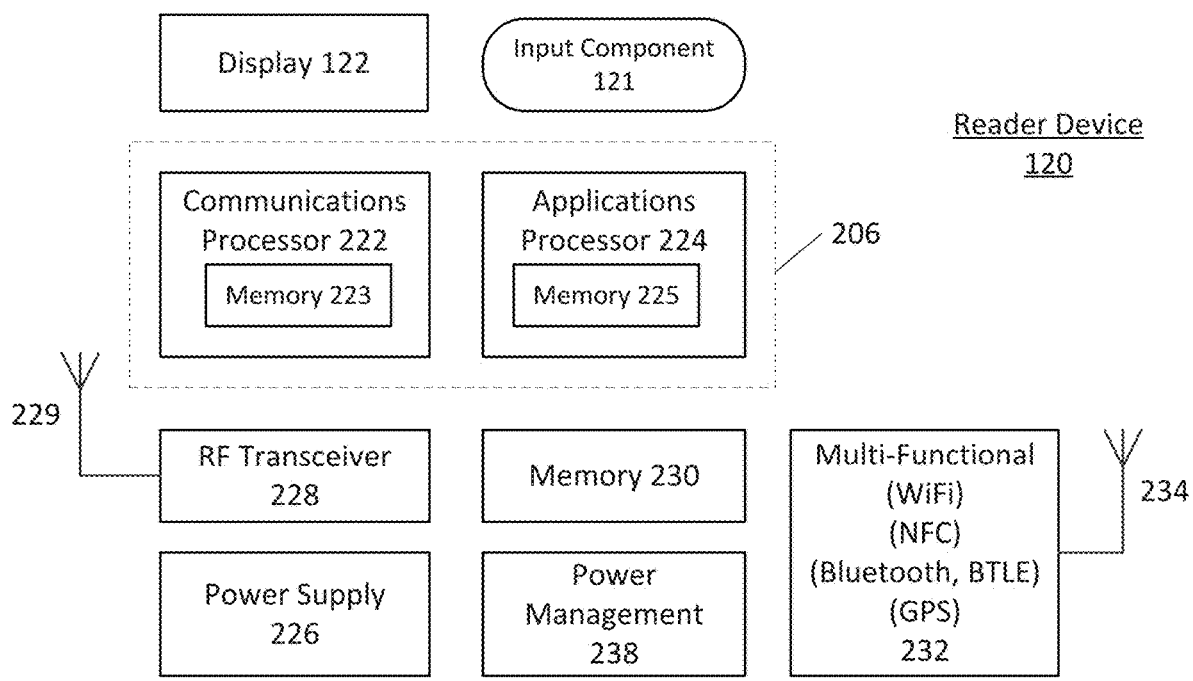
FIG. 2A is a block diagram depicting an example embodiment of a reader device configured as a smartphone.
Figure 2B:
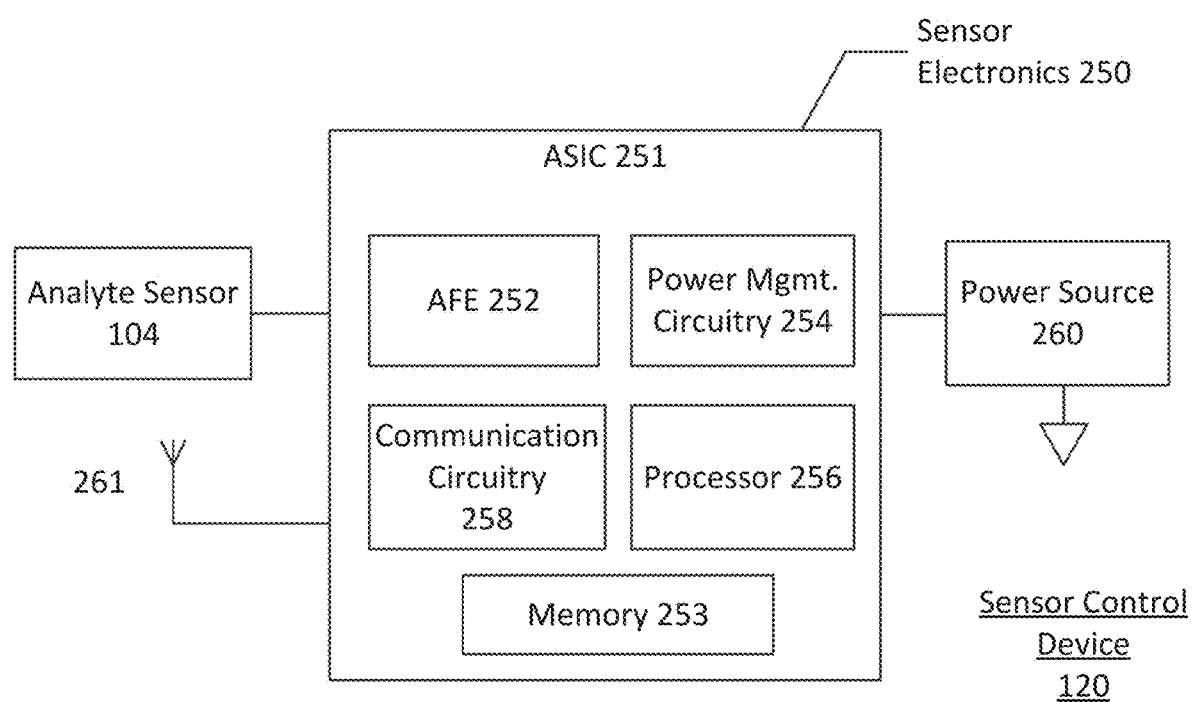
FIG. 2B is a block diagram depicting an example embodiment of a sensor control device.

FIGS. 2A-2B depict example embodiments of reader device 120 and sensor control device 102, respectively. As discussed above, reader device 120 can be a mobile communication device such as, for example, a Wi-Fi or internet enabled smartphone, tablet, or personal digital assistant (PDA). Examples of smartphones can include, but are not limited to, those phones based on a WINDOWS operating system, ANDROID operating system, IPHONE operating system, PALM WEBOS, BLACKBERRY operating system, or SYMBIAN operating system, with network connectivity for data communication over the internet or a local area network (LAN).

Reader device 120 can also be configured as a mobile smart wearable electronics assembly, such as an optical assembly that is worn over or adjacent to the user's eye (e.g., a smart glass or smart glasses, such as GOOGLE GLASSES). This optical assembly can have a transparent display that displays information about the user's analyte level (as described herein) to the user while at the same time allowing the user to see through the display such that the user's overall vision is minimally obstructed. The optical assembly may be capable of wireless communications similar to a smartphone. Other examples of wearable electronics include devices that are worn around or in the proximity of the user's wrist (e.g., a watch, etc.), neck (e.g., a necklace, etc.), head (e.g., a headband, hat, etc.), chest, or the like.

FIG. 2A is a block diagram of an example embodiment of a reader device 120 according to various embodiments disclosed herein. In this example, the reader device 120 is in the form of a smartphone, upon which the various software, applications, and graphical user interfaces disclosed herein can reside. Here, reader device 120 includes an input component 121, display 122, and processing hardware 206, which can include one or more processors, microprocessors, controllers, and/or microcontrollers, each of which can be a discrete chip or distributed amongst (and a portion of) a number of different chips. Here, processing hardware 206 includes a communications processor 222 having on-board non-transitory memory 223 and an applications processor 224 having on-board non-transitory memory 225. Reader device 120 further includes an RF transceiver 228 coupled with an RF antenna 229, a memory 230, multi-functional circuitry 232 with one or more associated antennas 234, a power supply 226, and power management circuitry 238. FIG. 2A is an abbreviated representation of the internal components of a smartphone, and other hardware and functionality (e.g., codecs, drivers, glue logic, etc.) can of course be included.

Communications processor 222 can interface with RF transceiver 228 and perform analog-to-digital conversions, encoding and decoding, digital signal processing and other functions that facilitate the conversion of voice, video, and data signals into a format (e.g., in-phase and quadrature) suitable for provision to RF transceiver 228, which can then transmit the signals wirelessly. Communications processor 222 can also interface with RF transceiver 228 to perform the reverse functions necessary to receive a wireless transmission and convert it into digital data, voice, and video.

Applications processor 224 can be adapted to execute the operating system and any software applications that reside on reader device 120 (such as any sensor interface application or analyte monitoring application that includes, e.g., SLL 304), process video and graphics, and perform those other functions not related to the processing of communications transmitted and received over RF antenna 229. Any number of applications can be running on reader device 120 at any one time, and will typically include one or more applications that are related to a diabetes monitoring regime, in addition to the other commonly used applications that are unrelated to such a regime, e.g., email, calendar, weather, etc.

Memory 230 can be shared by one or more of the various functional units present within reader device 120, or can be distributed amongst two or more of them (e.g., as separate memories present within different chips). Memory 230 can also be a separate chip of its own. Memory 230 is non-transitory, and can be volatile (e.g., RAM, etc.) and/or non-volatile memory (e.g., ROM, flash memory, F-RAM, etc.).

Multi-functional circuitry 232 can be implemented as one or more chips and/or components, including communication circuitry, that perform other functions such as local wireless communications (e.g., Wi-Fi, Bluetooth, Bluetooth Low Energy) and determining the geographic position of reader device 120 (e.g., global positioning system (GPS) hardware). One or more other antennas 234 are associated with both the functional circuitry 232 as needed.

Power supply 226 can include one or more batteries, which can be rechargeable or single-use disposable batteries. Power management circuitry 238 can regulate battery charging and power supply monitoring, boost power, perform DC conversions, and the like. As mentioned, reader device 120 may also include one or more data communication ports such as USB port (or connector) or RS-232 port (or any other wired communication ports) for data communication with a remote computer system 170 (see FIG. 1), or sensor control device 102, to name a few.

FIG. 2B is a block schematic diagram depicting an example embodiment of sensor control device 102 having analyte sensor 104 and sensor electronics 250 (including analyte monitoring circuitry). Although any number of chips can be used, here the majority of the sensor electronics 250 are incorporated on a single semiconductor chip 251 that can be, e.g., a custom application specific integrated circuit (ASIC). Shown within ASIC 251 are several high-level functional units, including an analog front end (AFE) 252, power management circuitry 254, processor 256, and communication circuitry 258 (which can be implemented as a transmitter, receiver, transceiver, passive circuit, or otherwise according to the communication protocol). In this embodiment shown in FIG. 2B, both AFE 252 and processor 256 are used as analyte monitoring circuitry, but in other embodiments either circuit can perform the analyte monitoring function. Processor 256 can include one or more processors, microprocessors, controllers, and/or microcontrollers.

A non-transitory memory 253 is also included within ASIC 251 and can be shared by the various functional units present within ASIC 251, or can be distributed amongst two or more of them. Memory 253 can be volatile and/or non-volatile memory. In this embodiment, ASIC 251 is coupled with power source 260, which can be a coin cell battery, or the like. AFE 252 interfaces with in vivo analyte sensor 104 and receives measurement data therefrom and outputs the data to processor 256 in digital form, which in turn processes the data to arrive at the end-result analyte discrete and trend values, etc. This data can then be provided to communication circuitry 258 for sending, by way of antenna 261, to reader device 120 (not shown) where further processing can be performed by, e.g., the sensor interface application. It should be noted that the functional components of ASIC 251 can also be distributed amongst two or more discrete semiconductor chips.

Performance of the data processing functions within the electronics of the sensor control device 102 provides the flexibility for system 100 to schedule communication from sensor control device 102 to reader device 120, which in turn limits the number of unnecessary communications and can provide further power savings at sensor control device 102.

Information may be communicated from sensor control device 102 to reader device 120 automatically and/or continuously when the analyte information is available, or may not be communicated automatically and/or continuously, but rather stored or logged in a memory of sensor control device 102, e.g., for later output.

Data can be sent from sensor control device 102 to reader device 120 at the initiative of either sensor control device 102 or reader device 120. For example, in many example embodiments sensor control device 102 can communicate data periodically in an unprompted or broadcast-type fashion, such that an eligible reader device 120, if in range and in a listening state, can receive the communicated data (e.g., sensed analyte data). This is at the initiative of sensor control device 102 because reader device 120 does not have to send a request or other transmission that first prompts sensor control device 102 to communicate. Broadcasts can be performed, for example, using an active Wi-Fi, Bluetooth, or BTLE connection. The broadcasts can occur according to a schedule that is programmed within device 102 (e.g., about every 1 minute, about every 5 minutes, about every 10 minutes, or the like). Broadcasts can also occur in a random or pseudorandom fashion, such as whenever sensor control device 102 detects a change in the sensed analyte data. Further, broadcasts can occur in a repeated fashion regardless of whether each broadcast is actually received by a reader device 120.

System 100 can also be configured such that reader device 120 sends a transmission that prompts sensor control device 102 to communicate its data to reader device 120. This is generally referred to as "on-demand" data transfer. An on-demand data transfer can be initiated based on a schedule stored in the memory of reader device 120, or at the behest of the user via a user interface of reader device 120. For example, if the user wants to check his or her analyte level, the user could perform a scan of sensor control device 102 using an NFC, Bluetooth, BTLE, or Wi-Fi connection. Data exchange can be accomplished using broadcasts only, on-demand transfers only, or any combination thereof.

Accordingly, once a sensor control device 102 is placed on the body so that at least a portion of sensor 104 is in contact with the bodily fluid and electrically coupled to the electronics within device 102, sensor derived analyte information may be communicated in on-demand or unprompted (broadcast) fashion from the sensor control device 102 to a reader device 120. On-demand transfer can occur by first powering on reader device 120 (or it may be continually powered) and executing a software algorithm stored in and accessed from a memory of reader device 120 to generate one or more requests, commands, control signals, or data packets to send to sensor control device 102. The software algorithm executed under, for example, the control of processing hardware 206 of reader device 120 may include routines to detect the position of the sensor control device 102 relative to reader device 120 to initiate the transmission of the generated request command, control signal and/or data packet.

Embodiments Associating Analyte Levels with Meal Information

In many embodiments, the subject matter described herein is implemented by a software application program that is stored on and executed by a processor-based device, such as any one of the reader devices, drug delivery devices, or other computing devices described herein. In certain embodiments, the software is implemented as one or more downloadable software applications ("an App") on a reader device such as a mobile communication device or smartphone.

The software can provide a mechanism for the user to define consumables (e.g., a type of food, type of drink, or portion thereof), in any fashion that is convenient to the user. These consumables will be referred to generally herein as a meal or meals, and these terms are used broadly to denote all types of food and drink.

This software can perform a number of functions related to the collection of meal information and association of that meal information with analyte information collected by in vivo analyte sensor 104 or by in vitro test strip and meter. The software will be generally referred to herein as the "meal monitor application."

The meal monitor application can allow an individual to log information about each meal that the individual consumes (i.e., each "meal event"), including a photo of the meal. The meal monitor application can associate analyte data from the same general time period where the user's log entry indicated that a meal was consumed.

The meal monitor application can also monitor the user's analyte data and identify when the analyte data changes in a manner indicating or suggesting the occurrence of a potential meal event and seek to associate meal information from the same general time period with that potential meal event. The meal monitor application can prompt the individual for confirmation that the potential meal event occurred and for information describing the meal event. If the individual has already entered meal information, then the system can prompt for additional information about the meal event that the user has not already entered. In some embodiments, if a meal has been detected, and the meal monitor application determines that meal information has already been entered, then the user may not be prompted.

The meal monitor application can also associate the measured analyte response with each meal event and store the result in a non-transitory memory or a database, regardless of whether the analyte response is also classified as or includes an analyte excursion. The meal monitor application can display each meal with its associated analyte (e.g., glucose or other analyte) response to the user, for example, as a list where each meal is sorted by descending degree of, using glucose as an example, glycemic response magnitude. The meal monitor application can display other lists, such as a list of "good" meals made up of meals where the glycemic response magnitude was below a predefined magnitude and/or made up of a number of meals that had the lowest magnitudes of all the meals recorded. Another example is a list of "bad" meals made up of meals where the glycemic response magnitude was above a predefined magnitude and/or made up of a number of meals that had the highest magnitudes of all the meals recorded.

One example embodiment of the glucose response magnitude is the peak glucose value detected from the glucose response after a meal. Methods for determining this peak glucose metric are described further herein. Another example embodiment of the glucose response magnitude is the difference from the peak glucose value after a meal and the glucose value at the start of the detected meal.

In yet another example embodiment, the glucose response magnitude may be determined from a form of "area under the curve." The system can determine the value of the area with an upper bound set by a trace or curve along (or approximating) the values of the collected glucose data from the start of the detected meal and ending upon or after a) a fixed time such as 6 hours, b) the start of the next detected meal, c) an occurrence when the glucose trace falls below the value of the start of the meal, In one example embodiment the end point is whichever of the preceding events (a-c) occurs first. The lower bound for the area determination can be the glucose value at the start of the detected meal. The area can be calculated by summing the glucose values between the start and the end (inclusive or exclusive) and multiplying this sum by the total time from start to end, then subtracting the glucose value at the start of the detected meal multiplied by the total time from start to end. Other similar magnitude metrics along these lines can be implemented.

If the user consumes the same or a similar meal on repeated occasions, then a glycemic central tendency (e.g., an average or median glycemic response) can be determined for that meal and that central tendency can be displayed. For example, if the peak of the glycemic response is the metric of choice, then when multiple identical meals have been recorded by the system, the median of the peak values can represent the glycemic response metric for this meal. Other forms of glucose response metrics such as a glucose trace or a parametric fit to the glucose trace, may be used. Alternatively, the glycemic response of every meal can be displayed regardless of whether each meal is the same or similar to another meal on the list or in the database. In yet another alternative embodiment, the meal monitor application may generate a glycemic response as representative of all similar meals; for instance, if the glycemic response is displayed as a trace, the trace representative of all the similar meals may be made up of hourly medians of all of the individual glycemic responses, where time is relative to the start of the meal.

Example embodiments of the meal monitor application can utilize analyte data analysis software or software implementable processes, for example, as disclosed in any of U.S. Patent Publication Nos. 2013/0085358, 2014/0350369 or 2014/0088393, or in Int'l Publ. No. WO 2015/153482, all of which are incorporated herein in their entirety and for all purposes. Example embodiments of this software are collectively referred to herein as the "meal event detector." The meal event detector can be an algorithm, routine, or other set of instructions (part of or separate from the meal monitor application) that can detect and/or quantify the occurrence of an actual or potential meal event in the individual's monitored analyte data.

Detection of a meal event can include detection of analyte episodes or excursions outside a desired acceptable (e.g., medically recommended) target range in the user, who can be informed by the software that one or both has been detected. Examples of analyte excursions include violation of a low glucose threshold, violation of a high glucose threshold, violation of a rate of change (e.g., increase or decrease) threshold, violation of a glucose median threshold, violation of a glucose variability threshold, and the like.

Some of the meal event detectors described in these incorporated references are described only in terms of identifying analyte excursions outside a desired target range. These embodiments can be extended to the detection of meal events based on the teachings contained within other ones of these incorporated references (e.g., Int'l Publ. No. WO 2015/153482). These embodiments can also be extended to the detection of meal events by specification of a within-target episode, where glucose values are maintained between an upper and lower bound for a period of time. Detection of these episodes can be done by extension of threshold-based episode detection algorithms.

A relatively straightforward example of threshold-based logic includes grouping all consecutive points above or below a threshold into a grouping to be associated with the meal event, which can, in some instances, also be or include an analyte excursion outside of the user's targeted acceptable range.

Very brief episodes (e.g., trends or groupings in the analyte data or outlier values) may not be clinically relevant. Embodiments described herein can manage this challenge by requiring a minimum number of readings and/or a minimum duration and/or a minimum area (e.g., an integration) outside the threshold to consider the episode for analysis as either a meal event or an analyte excursion. An episode failing any of the requirements may be ignored. Software displays and applications for providing upload prompts to an individual are disclosed in the incorporated reference US 2014/088393, which also discloses software applications for providing heuristic meal announcements that can be used herein for analysis and display of data as well as for meal selection.

A virtually limitless catalog of analyte episode types exist (e.g., analyte data occurrences having different characteristics), each of which, if independently clinically relevant, can be used to form the basis for meal reports, meal effects, meal analysis, meal-based treatment, medication administration, and meal selection. Glycemic response and episode characteristics can also be used to classify meals and certify meal-related collected data. Such analysis and results can be presented to the individual, clinical meal supervisor, or physician to make future meal decisions.

Figure 3A:
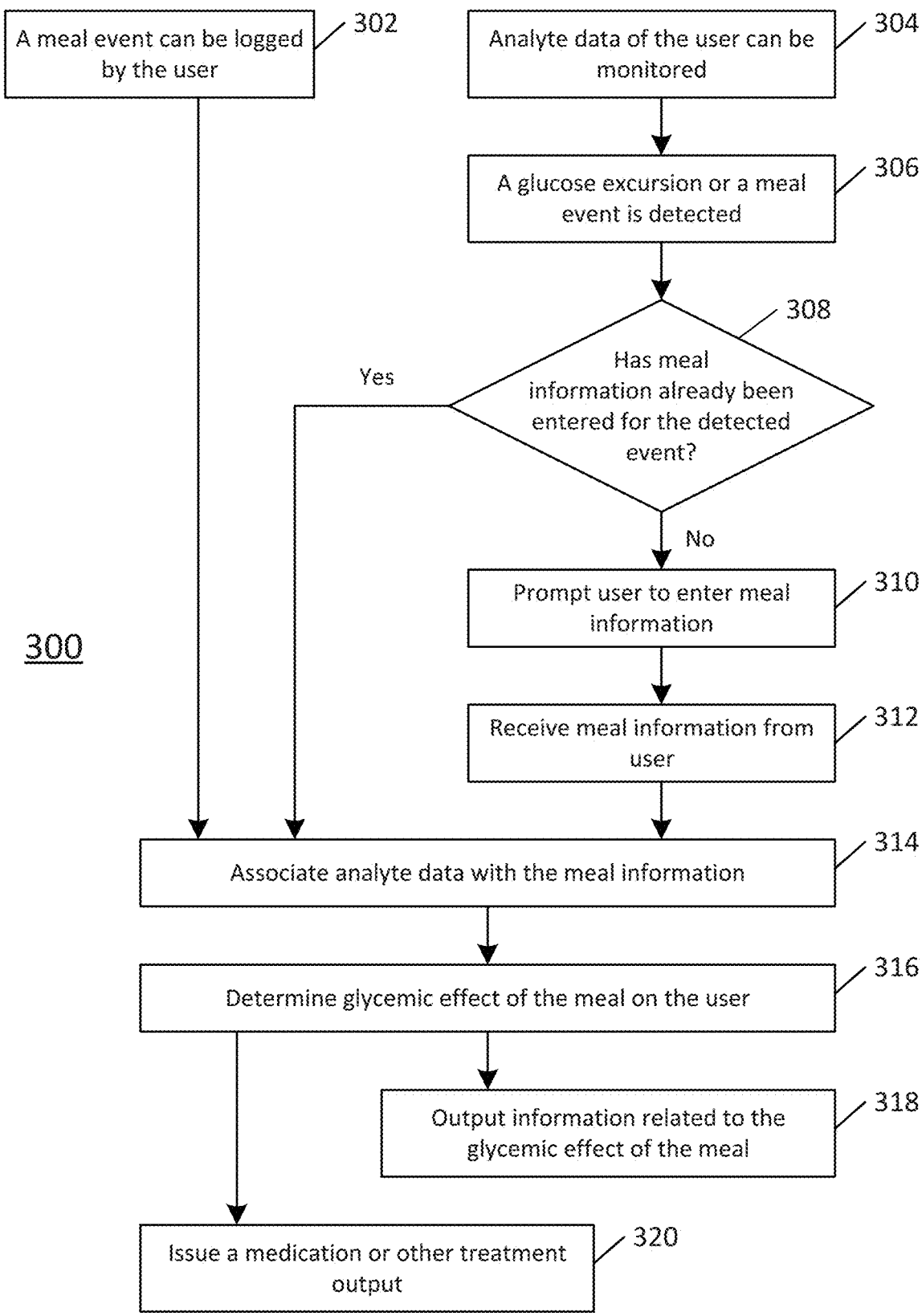
FIG. 3A is a flow diagram depicting an example embodiment of a method for meal information gathering and assessment.

Reference is now made to FIG. 3A, which is a flow diagram depicting an example embodiment of a method 300 for meal information collection, association with analyte data, and determination of glycemic impact of that meal. Method 300 includes acts that may be described as performed by an electronic device, such as reader device 120, drug delivery device 160, or computer system 170 or 180, or processors thereof. The user may be an individual or diabetic sufferer, clinical administrator, medical professional, dietary profession, or other person. By way of example only, method 300 will be described by reference to a diabetic using the meal monitor software as a downloaded app on a reader device 120 configured as a smart phone. For ease of illustration, the monitored analyte in this and other embodiments described below will be glucose, although other analytes can be monitored as well as is noted herein.

Referring to FIG. 3A, a meal event can be logged by the user at 302. The user can input meal information directly into reader device 120 (via a user interface) at his or her own discretion, before, during, or after consumption of the meal. In some embodiments, the user inputs meal information in response to a reminder generated by the meal monitor application according to a predetermined schedule, which can be set and/or modified by the user. Example embodiments of user interfaces for accepting a manual log by the user are described with respect to FIGS. 4A and 4B.

Analyte data of the user is monitored at 304. This monitoring, in most embodiments, is a continuous process (e.g., a frequently repeated process, automatically or at the discretion of the user) that is ongoing so long as the user is wearing sensor control device 102. Data collected by sensor control device 102 can be transferred to reader device 120 such that the meal monitor application has access to the data. Information indicative of the time at which each analyte data measurement is collected (e.g., a timestamp) can also be transferred to reader device 120. As already described herein, this data transfer can occur in an on-demand fashion (e.g., the performance of a scan by the user) or in a broadcast or other regularly occurring fashion. Analyte data collected by a discrete blood glucose measurement (e.g., such as the reading of a test strip with a meter) can also be entered into reader device 120 manually or automatically.

Reader device 120 can algorithmically process the collected analyte data and determine whether a glucose excursion or a meal event has occurred at 306. This can occur by use of a meal event detector as described herein, which examines the analyte data for one or more analyte values that violate a threshold or other condition that is indicative of the occurrence of a glucose excursion or a meal event. This algorithmic processing can likewise be frequently repeated, e.g., each time new analyte data is received from sensor control device 102, such as in response to a user performed NFC scan of sensor control device 102 with reader device 120 or otherwise. The manual logging of meal information by the user (302) can occur contemporaneously with the monitoring (304) and processing (306) of the analyte data.

Each time new data is transferred to reader 120, the algorithmic processing can be applied to the new data, which might represent a multiple hour time period (such as the last 8 hours) to detect meal events. Steps 308-320 can be performed for each meal that is detected, starting with the most recent detected meal and repeating for every other detected meal event.

In some example embodiments, the meal event detector can use a one or more sets of predefined glucose rate of change (e.g., rise) settings to attempt to detect all meals in the analyte data. If analyte data exceeds the rate of change threshold, such as a series of data points over a predetermined time range where the average increase in value from one point to the next exceeds a threshold, then that analyte data can be characterized as a glucose excursion.

One problem that specifically arises from the use of the meal monitor application is that the meal monitor application may be either too sensitive or not sensitive enough to analyte data that suggests the occurrence of a meal event. This problem can result in the identification of too many or not enough meal events.

In some embodiments, the settings that are used by the meal event detector to determine whether a potential meal event has occurred can be adjusted. For example, each setting or threshold used by the meal event detector can be individually set by the user. In another embodiment, the meal monitor software can provide the ability to scale the sensitivity of the settings, for example by providing the option for the user to select one of a plurality of different settings each having a different magnitude.

The meal monitor software can default to a "medium" (or "normal" or "default") mode using a group of predetermined settings or the settings input by the user. The meal monitor software can provide the option to switch to a different mode, such as a "low" mode or a "high" mode where the sensitivity or magnitude of the settings are scaled to be less likely or more likely, respectively, as compared to the "medium" mode, to consider a particular span of analyte data to qualify as a potential meal event. The "low" mode and "high" mode can each be a direct percentage scaling of the settings of the "medium" mode. For example, the "low" mode may use the settings of the "normal" mode adjusted by 5%, 10%, 15%, 20%, 25%, etc., so as to decrease the likelihood that a meal event is detected. Likewise, for example, the "high" mode may use the settings of the "normal" mode adjusted by 5%, 10%, 15%, 20%, 25%, etc., so as to increase the likelihood that a meal event is detected. While three setting options are described here any number of two or more setting options can be used. Also, the meal monitor software application can provide the option for the user to scale the sensitivity of the meal event detector in an analog or virtual-analog fashion (at least from the user's perspective), such as with a slide bar on a touchscreen.

In some embodiments, the meal monitor application is self-monitoring and optionally self-correcting, such that sensitivity of the meal event detector can be continually or repeatedly monitored against a desired baseline and, if it appears that the sensitivity of the meal event detector requires adjustment, then the user can be notified to make an adjustment or the meal monitor application can automatically adjust itself without input from the user.

Figure 3B:
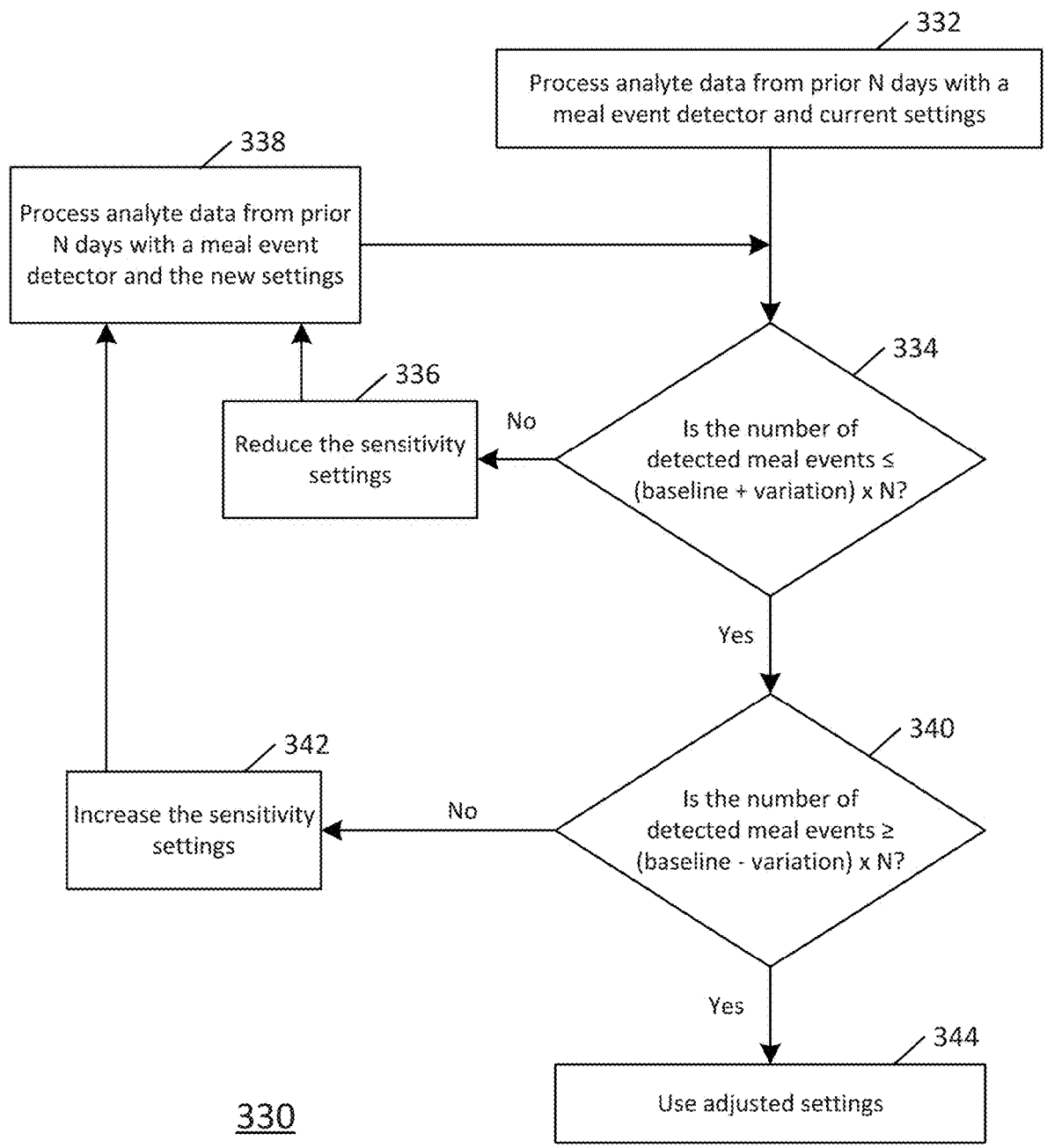
FIG. 3B is a flow diagram depicting an example embodiment of a method for performing automatic meal detection sensitivity setting adjustments.

FIG. 3B is a flow chart depicting an example embodiment of method 330 for automatically adjusting the sensitivity of the meal event detector. Here, method 330 can utilize a baseline integer or decimal value indicative of the normal number of meals the user consumes each day. This baseline value can be set by the user or can be a default value (e.g., one, two, three, four, five, etc.) set within the meal monitor application. Method 330 can also utilize a variable integer or decimal value that can account for typical variation in the daily number of meals that the user consumes.

In this embodiment of method 330, the meal monitor application runs the meal event detector on the analyte data from a prior time range (e.g., N days, hours, minutes) using a first set of sensitivity settings (e.g., analyte data magnitude thresholds, duration thresholds, rate of change thresholds, or others) at 332. Here, method 330 examines the analyte data over the previous N days, where N can be any desired value. Next, a determination is made at 334 whether the number of meal events detected over those N days is less than or equal to a maximum, which in this embodiment is (the baseline value added to the variation value) multiplied by N. In an example where N is three, the baseline value is three meals/day, and the variation value is one meal/day, then the determination at 334 would evaluate whether the number of meal events detected is less than or equal to twelve (e.g., the maximum).

A determination that the number of meal events is greater than the maximum indicates that the meal event detector settings are too sensitive. Thus the routine of method 330 proceeds to 336 where the sensitivity settings are reduced. Reduction of the sensitivity settings can be to the next lowest set of predetermined sensitivity settings, or can be by a scaling factor such as by 1%, 2%, 5%, 10%, etc. Then, at 338, the meal event detector is performed on the analyte data from the prior time range with the new settings. Method 330 then proceeds to make the determination at 334 again. The process can repeat until the sensitivity settings are reduced sufficiently so as to not to violate the condition of 334.

When the condition of 334 is passed (e.g., the detected number of meal events is less than or equal to 12), the routine proceeds to make a determination at 340 as to whether the detected number of meal events is greater than or equal to a minimum, which in this embodiment is (the variation value subtracted from the baseline value) multiplied by N. In the example where N is three, the baseline value is three meals/day, and the variation value is one meal/day, the determination at 340 would evaluate whether the number of meal events detected is greater than or equal to six (e.g., the minimum).

A determination that the number of meal events is less than the minimum indicates that the meal event detector settings are not sensitive enough. Thus the routine of method 330 proceeds to 342 where the sensitivity settings are increased. Increase to the sensitivity settings can be to the next highest set of predetermined sensitivity settings, or can be by a scaling factor such as by 1%, 2%, 5%, 10%, etc. The routine then proceeds to 338 where the meal event detector is performed on the analyte data from the prior time range with the new settings. Method 330 then proceeds to make the determination at 334 again and the process can repeat until the sensitivity settings are adjusted sufficiently so as to not to violate the conditions of 334 and 340. When the condition of 340 is met, the routine proceeds to 344 where the adjusted settings are considered to be appropriate and are used in the subsequent normal course of operation of the meal event detector.

Method 330 can be repeated at regular intervals. In one example embodiment, method 330 is performed once per day using data from the prior N days as measured from midnight to midnight to prevent the settings from changing multiple times per day.

In another embodiment, the meal monitor application can perform an automated sensitivity adjustment that analyzes the data to identify settings that are too high without regard to whether the settings are too low. For example, a self-adjustment routine can iteratively assess whether each of a plurality of settings is beneath a maximum by starting with the highest setting, determining whether the meal event detector outputs a number of detected meal events that is less than the maximum using the highest setting and if so, then using those highest settings for subsequent normal operation of the meal event detector. If the highest settings result in a number of detected meal events that exceeds the maximum, then the routine can proceed in order of decreasing magnitude through each iteratively lower setting and stopping when a setting is identified that does not exceed the maximum. That identified setting can be used for subsequent normal operation. In yet another embodiment, the meal monitor application can perform an automated sensitivity adjustment that analyzes the data to identify settings that are too low, without regard to whether the settings are too high, in a similar but reverse fashion.

Referring back to FIG. 3A, if a glucose excursion or meal event is detected at 306, then, at 308, the meal monitor application assesses whether meal information has already been entered (such as by the user at 302) that corresponds to the detected glucose excursion or meal event (collectively referred to as the "detected event"). This assessment can be performed by examining a period of time before, and optionally to a limited extent after (e.g., to compensate for inaccuracies in time keeping or entry), the times at which the detected event occurred to see if any meal information was entered during that time period. If so, then the meal monitor application can associate that meal information with the detected event at 314. If multiple meal information entries are found, then the meal monitor application can associate all with the detected event, or can associate the detected event with only the meal information which occurred closest in time.

If no meal information has been entered that can be associated with the detected event, then at 310, the user is prompted to enter the meal information. Example embodiments of user interfaces for prompting the user to log a meal or meal information are described with respect to FIGS. 4C-E. If no meal event has occurred, the user can decline or ignore the prompt. Otherwise, the meal information can be entered at 312.

Prompting can take the form of an alarm notification, such as a vibration or sound that clues the user into activating the meal monitor application to see the prompt. Alternatively, the prompt may be a notification that appears when the user next views the application.

Regardless of whether the user logs meal information at his or her own discretion (302) or in response (312) to a prompt (310), the meal information can include various levels of detail and can be entered in the same or similar fashion.

A desirable aspect of the embodiments described herein is the ease at which meal information can be entered so as to promote usage of the meal monitor application to gain a more intuitive understanding of glycemic impact of meal consumption, which in turn can improve the user's health. The meal information can be input in any desired manner, such as by the manual entry of text, by selection of the meal name from a list (e.g., a picklist or drop-down list), by selection of the meal picture from a group of pictures, by selection of recognizable indicia (e.g., a tag or code) of the meal, or any combination thereof.

The meal information can include a meal type, for example, whether the meal is breakfast, lunch, snack, dinner, or dessert, etc. The meal information can include the time range (e.g., start time and stop time) during which the meal was consumed. This can be an actual time (e.g., a start time in hour:minutes) or can be a generalized or heuristic part of the day (e.g., early morning, late afternoon, etc.), or an approximated time range (e.g., 6-7 am, 5-6 pm, etc.) with any desired level of granularity of the time range (e.g., 10 minute, 15 minute, 30 minutes, 60 minutes, etc.).

The meal information can also include the contents and portion sizes of the meal. For example, the meal may be described as including a caloric amount, protein, carbohydrates, dairy, meat, grain, vegetables, nuts, sugar, alcohol or other beverage type, etc. along with the respective amount or size for each content. This can be done on a portion by portion basis, for example, one serving of bread with one serving of peanut butter, where each portion has the respective amount of carbohydrates, sugar, protein, etc. associated with it. Alternatively, the meal may be described on solely a nutritional category basis, for example, 10 grams of carbohydrates, 5 grams of sugar, 8 grams of protein, etc. Heuristic categories (e.g., small portion, medium portion, large portion) as opposed to quantitative categories can also be used to facilitate data entry.

To further facilitate the entry of meal information, the meal monitor application can present options from which the user may select meals or information about meals. For example, meals or meal information can be presented to the user in the form of a list or array from which the user can select the most appropriate entry that describes the meal consumed by the user.

In some embodiments, the user can create a list or array of common meals consumed by the user (and/or associated information) for use by the meal monitor application, either by directly entering the list into the application, by selecting from a list of options preprogrammed into the meal monitor application, or by creating the list on a separate computing platform and uploading it to the host device on which the meal monitor application is being executed. Consumables can be added or removed at any time. As discussed herein, this data entry can be performed using a graphical user interface on the host device.

The meal monitor application can be programmed to store the information about any and all prior meals and associated meal information previously consumed by the user. That information can be presented to the user as options from which the user can select to identify a particular meal or aspect thereof that was more recently consumed. For example, when the user is prompted to enter meal information, the meal monitor application can present a list of options from which the user can choose. This list can be ordered such that the most commonly consumed or selected meals are presented first or at the top of the list, with remaining meals presented in order of decreasing frequency of consumption (e.g., the most commonly consumed meal is presented first, the second most commonly consumed meal is presented second, and so forth with the least commonly consumed meal presented at the end).

The user may often need to tailor a selected meal based on the occasion. Thus, for any meal selected, the user is given the option to customize an aspect of that meal, such as by the addition, removal, or substitution of a particular side (e.g., substitution of broccoli for peas) or drink, modification to a portion size, modification to a caloric or carbohydrate content, and so forth. In any and all instances where the user enters information about a selected meal, a similar approach can be taken where the user is provided with a list of options from which to choose, the options being presentable in order of most relevant to least relevant. For example, if a particular type of food is selected, previously consumed portion sizes of that particular type of food can be presented to the user. Again this can be done in descending order based on frequency of consumption. For example, if chicken breast is selected as part of a meal, then based on the user's prior history stored on the device, the meal monitor application may present portion sizes to choose from in order of descending frequency of consumption (e.g., 8 ounces, 10 ounces, 6 ounces). Or the list may be presented in increasing (least to most) or descending (most to least) order of portion size. The same applies, for example, with respect to carbohydrate amount, sugar amount, protein amount, and any other aspect of meal information described herein.

Thus, selection of a particular meal can be followed by entry of information about each type of food and drink within that meal where the user's history can be used to present the most relevant options first. Of course, if no customization is required, the user can end the data entry process after initial selection of the meal itself without further specifying variations in portion sizes etc.

The meal monitor application can be programmed to filter the presentation of options based on the time of day. For example, if the user is prompted to enter information about a meal consumed during morning hours, the meal monitor application can present a list of the commonly consumed breakfast meals and/or morning snacks, etc. (in order of descending frequency of consumption) such that the user is provided only the most relevant options from which to choose (e.g., dinners are excluded). Similarly, when entering information about meals consumed in the middle of the day, only the most commonly consumed lunches and/or afternoon snacks can be presented and, when entering information about meals consumed late in the day or in the early evening, only the most commonly consumed dinners, desserts, and/or evening stacks can be presented.

The meal monitor application can also be programmed to filter the presentation of options based on the characteristics of the detected event (e.g., the magnitude and/or duration of glucose excursion or meal event) and/or the correlation between the characteristics of the detected event and prior meals associated with detected events having similar characteristics. For example, the meal monitor application can have local access (e.g., stored in local memory) or remote access (e.g., by downloaded from a server) to the user's historical glucose levels over the previous amount of time, e.g., days, weeks, months, etc., as well as meal information entered into system 100 over that same or similar amount of time.

When a meal event is detected, the meal monitor application can identify prior detected events with the same or similar characteristics in the analyte data. This can be done by reference to a database of correlations stored locally or remotely to the meal monitor application within system 100. When the user is prompted to enter meal information based on a detected event, the meal monitor application can present meal options for selection based on the correlation between the analyte data of the recently detected event and analyte data of previously detected events that already have meal information associated therewith. Time of day information can also be used in the correlation. For example, if a hypoglycemic event is detected in the early evening, and previously detected hypoglycemic events occurring in the early evening were previously associated with a particular high carbohydrate meal (e.g., a spaghetti dinner), then the user may be presented with that particular high carbohydrate meal as the first option from which to select, followed by other options in order of decreasing potential relevance.

In other embodiments, when a meal event is detected, a list of all previous meals can be displayed to the user (or accessed by a virtual selectable button labelled, for instance, "previous meals"). The user can be permitted to select one meal as corresponding to the detected meal event. The list of all previous meals can be sortable by frequency of past selections of that meal and/or by magnitude or severity of the glycemic response to that meal, which can be an average or median value if that meal has been consumed multiple times in the past. The list may be ordered any number of ways, but the preferred embodiment is to order first by the most frequently selected meals, and next by the most recent meals. Each meal can be associated with a unique identifying code. Meal names that are entered by the user with text that is not identical but that resemble each other can be assigned the same code. If the same meal is entered and selected one or more times, that unique identifying code will be stored multiple times associated with the different times for this same meal. When displayed on a list sorted by glucose response magnitude, the meal monitor application can detect when meals are repeated by detecting that they have the same unique code. The meal monitor application can create a list of all the glucose responses for each repeated meal and determine the mean or median of these responses and associate this with the unique code. When this is done for all of the unique codes, then the final list for display can be generated for all of the unique meals including meals entered only once, and repeated meals, and the list can be sorted by the glucose response magnitude associated with each unique code.

If the user selects a meal event that is associated with an undesirable glycemic response, then a real-time notification can be generated and output to the user to warn that user of the potential glycemic impact of the meal that was just consumed.

Such real time feedback (i.e., feedback returned immediately from the user's perspective), can help the user internalize the undesirable effect of the consumed food. For example, if the type of meal event detected is a dinner meal, then the real-time notification can display the average glycemic response of all other meals of that type (dinner) along with the average glycemic response of the type of meal that was just consumed and an indication of the difference (e.g., the recently consumed meal has a typical glycemic response 20% higher than the average glycemic response of all other dinner meals). The real-time notification can also warn the user to eat less or take an offsetting medication such as insulin.

Figure 3C:
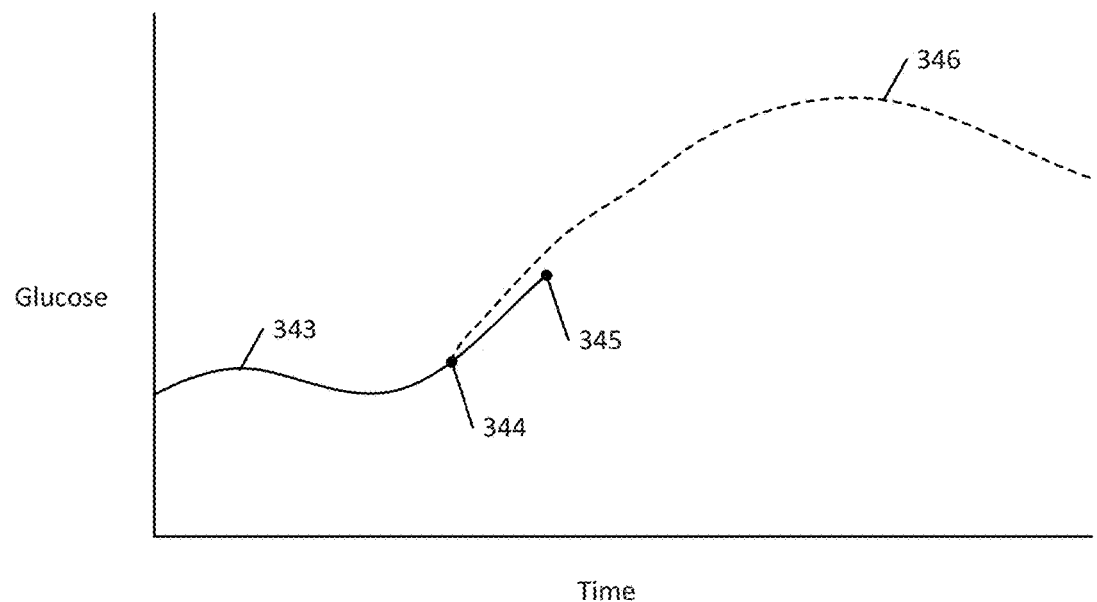
FIG. 3C is an example embodiment of a graphical display of a user's analyte data over time, with a superimposition of previous glycemic responses

In one example embodiment, the notification can include a graphical display of the user's current analyte data over time, with an average of all previous glycemic responses to that meal type superimposed on the current analyte data graph synchronized to the meal start time. One such example is depicted in FIG. 3C, where a trace 343 of the user's current analyte data is displayed over time. The meal start time is indicated at 344 and the last collected analyte measurement is indicated at 345. Upon selection of a meal type that is associated with one or more undesirable prior glycemic responses, the graph of FIG. 3C can be displayed with an overlaid trace 346 representing the average glycemic response in the user for all prior consumptions of the same meal type (or all previous times in which an undesirable excursion occurred with that meal type). The start of the overlaid trace 346 can be aligned with the analyte data at the meal start time 344. Thus the user is given real-time visual feedback of the likely result of consumption of that problematic food. Alternatively, multiple traces can be overlaid where each trace represents a single past excursion from consumption of that meal type.

Alternative outputs include reports that are available from a menu provided by the meal monitor application. Examples of reports include a list of detrimental meals (e.g., a "bad meal" list) and a list of beneficial meals (e.g., a "good meal" list). The bad meal list can be a list of previous meals sorted by descending glucose response magnitude, whereas the good meal list can be of previous meals sorted by ascending glucose response. The lists may be further modified by only including meals, for instance on the bad list, that exceed a predetermined or user defined threshold of glucose response magnitude. For the good list, only meals that are less than a predetermined or user defined threshold of glucose response magnitude can be included. Also, for the list of previous meals used to select from when entering meal information, symbols may be used to identify meals as good, bad or neither, as described above. Good and bad meals may be identified in other ways for this selection list, such as inclusion in respective sub-lists. Also, reports and periodic notifications may be provided that keep a running total of the quantity of good meals and bad meals over an elapsed period of time, such as one week or two weeks. For instance, each time the user selects this report, the meal monitor application can count the number of good meals and the number of bad meals and display the result. In addition, the application can provide a user interface that allows the user or health care provider to set a goal for the maximum number of bad meals in a period of time. The report display can show the current number of bad meals next to the goal. Alternatively, the application may generate periodic notifications regarding these metrics, where the period is, for instance, weekly.

The application can process new data (whenever available either automatically or when manually queried) to detect meals, measure glucose responses to detected meals, and perform the running calculation on the meals. Alternatively, the application can determine glucose responses whenever they are needed for analysis or reporting; that is, glucose responses are retrieved from memory but recalculated when needed. When the running calculation of, for instance, bad meals per week exceeds a threshold (or falls below a threshold), a notification can be generated indicating to the user that their eating habits have digressed (or congratulating that the goal has been met). Notifications may take the form of the those like a standard lock screen notification on Android and iOS phones, or they may be presented on specific display areas on common application screens such as the home screen or the glucose result screen.

The user has the option to input a photograph or image of the meal. This image may be entered to supplement other information also entered to describe the meal. Alternatively, this image can constitute the entire description of the meal and its contents. This streamlined data entry can greatly facilitate the ease at which the user enters data in logging a meal or responding to a prompt, thereby encouraging use of the meal monitor application. If an image is entered, that image can be presented along with or instead of a textual description of the meal and/or contents thereof, such that the user need only recognize the image in a list of options presented to the user for data entry. Thus, when the user is presented with options for identifying a meal in response to the detection of an event, those options can be presented solely in the form of text, solely in the form of icons, or solely in the form of images, or those options can be presented in a combination of text, icons, and/or images.

In some embodiments, the imagery of the meal can be analyzed using image recognition techniques to identify attributes of the meal such as recognizable components of the meal. The components of the meal may be recognized using meal component recognition algorithms based on spectral boundaries defined within the image. If recognized, the meal imagery can be given a name by the meal monitor application that describes the meal contents, e.g., a picture of chicken and broccoli can be labeled as "chicken and broccoli." The meal monitor application can then provide options to the user to specify further information, e.g., the portion amount, nutritional content, etc., for the particular type of meal detected from the imagery. That meal can also be linked to prior instances where the same type of meal occurred in the user's meal history and used in correlating detected events to particular types of meals.

FIGS. 4A-E depict example embodiments of graphical user interface (GUI) visual arrangements or screens. These screens can be displayed on any of the embodiments of reader device 120, drug delivery device 160, or local computer system 170 described herein.

Figures 4A, 4B:
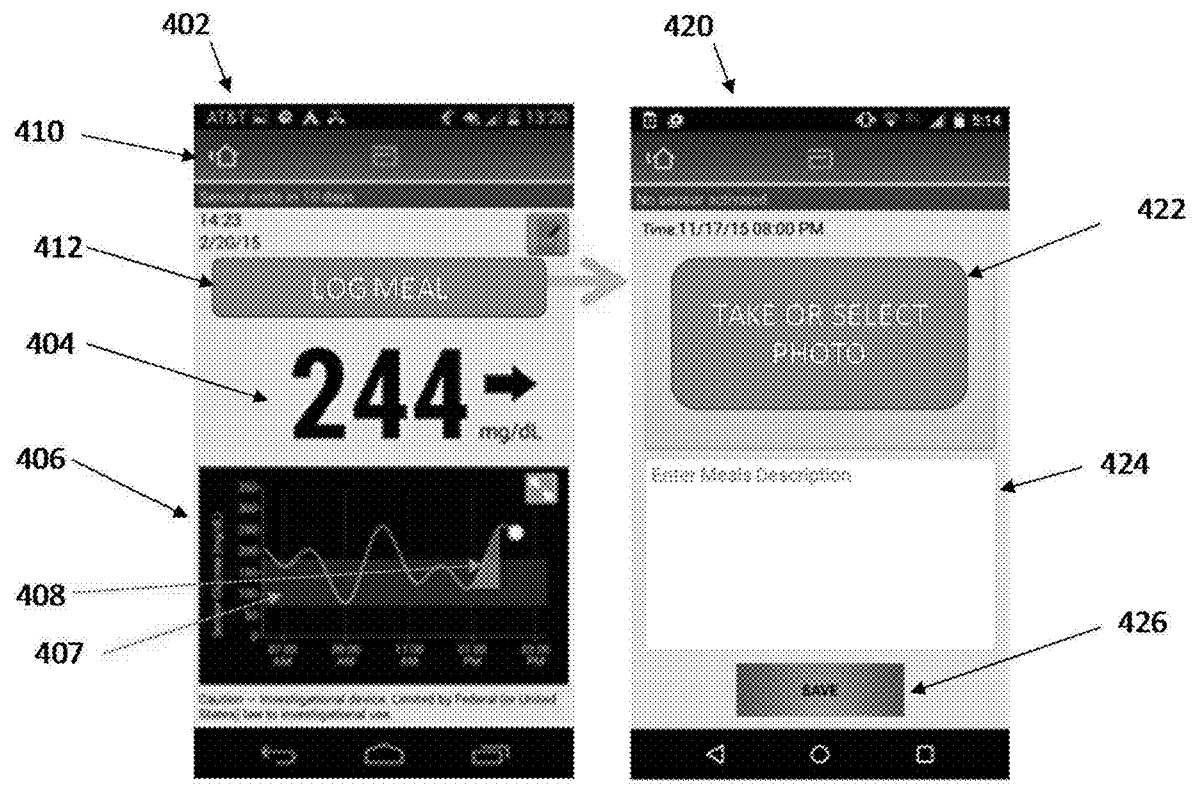

FIG. 4A depicts an example embodiment of a screen 402 for logging meals and associated meal information, for example, as would be used at 302 of method 300 (see FIG. 3A). Screen 402 can include indications 404 and 406 of analyte levels determined from data received from analyte sensor 104 (not shown). Indication 404 is a numerical display of the user's current or last received analyte level (e.g. mg/dL). Indication 406 is a graphical display depicting a trace or curve of the user's analyte level (y axis) over time (x axis) against a shaded region 407 indicative of normal or desired analyte level range. Such an indication 406 can show data over any desired time period (e.g., eight hours or other periods).

Screen 402 can include visual indicators for indicating various attributes of the data. For example, graphical display 406 can include a highlighted or otherwise accentuated indicator or marker 408 of the data. Here, indicator 408 is indicative of a glucose rate of change that exceeds a desired maximum rate of change, e.g., a rapid rise (or in other instances a rapid fall) of the analyte data over time. Specifically, indicator 408 is a highlighted area beneath the analyte level curve corresponding in time to the occurrence of the rapid rise. Thus, an observer can more readily appreciate whether recent events or excursions have occurred, as well as their nature.

Screen 402 can be a home screen for the meal monitor application or can be accessed from a home screen or other higher level page. Here, screen 402 is accessed from a home screen and includes a selectable home screen back button 410 to return thereto, which can likewise redirect back to any other higher level page.

Screen 402 also includes a Log Meal selectable button or field 412. Selection of the Log Meal button 412 can direct the user to screen 420 depicted in FIG. 4B. If the device on which the meal monitor application is operating includes a camera, then screen 420 can include a selectable Take or Select Photo button or field 422 that, upon selection, can open a camera application with access to the device's camera to capture a photograph or image of the meal for storage and association therewith. Selection of button 422 can also give the user the option to select a photo from a gallery of photos previously used to log meals, or from a gallery of photos stored in the device's general purpose photo gallery. If the user captures or otherwise selects a photo of the meal, then that photo can then be displayed on screen 420. In some embodiments, selection of Log Meal button 412 of FIG. 4A can cause the meal monitor application to immediately open the device camera application to allow the user to take a photo and thereby further streamline the image entry process.

Also included on screen 420 is a textual entry input location 424 for the user to enter free text information describing the meal. Selection of this location 424 opens a text editor which can be used to enter textual information about the meal. This information, along with the photograph, can be associated with the meal and can form part of a data structure representing the meal. Although not shown here, a pick list or drop-down list can also be included on screen 420 that the user can select to choose from a previously stored list of options for the meal or the meal's information, as described in detail herein.

Although not all variations are depicted, it is recognized that all aspects of meal information described herein can be input via one or more screens similar to those described with respect to FIGS. 4A and 4B, including, but not limited to, the entry of time of meal information, meal portion information, nutritional content, representative meal icons, and so forth.

After the meal information is entered, either with a photo, textual description, or selection of a predetermined option, the user can select a Save button or field 426 to save the data to memory, as a data structure associated with and digitally describing the meal.

Figures 4C, 4D, 4E:
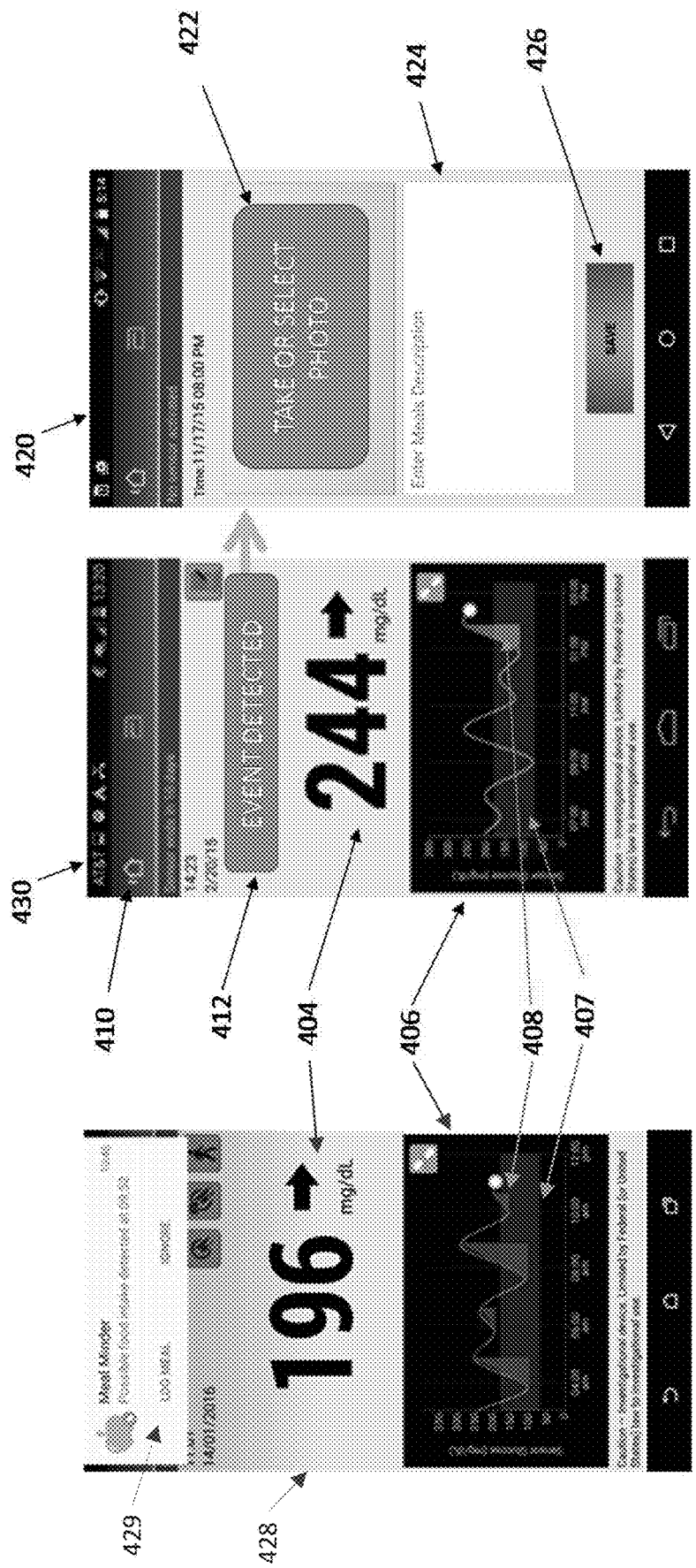

FIGS. 4C-E depict example embodiments of screens 428 and 430 for prompting a user to enter meal and associated meal information, for example, as would be used at 310 of method 300 (see FIG. 3A). Like screen 402 of FIG. 4A, screens 428 and 430 can include indications 404 and 406 of analyte levels determined from data received from analyte sensor 104 (not shown). Also like screen 402, indicator 408 is indicative of a glucose rate of change that exceeds a desired maximum rate of change, e.g., a rapid rise (or in other instances a rapid fall) of the analyte data over time. Specifically, indicator 408 is a highlighted area beneath the analyte level curve corresponding in time to the occurrence of the rapid rise.

This rapid rise can be the glucose excursion or meal event detected at 306 of method 300 (see FIG. 3A), which is the impetus to prompt the user at 310 to enter meal information. Screen 428 of FIG. 4C is an example of a home screen of the meal monitor application. Here, when an excursion or event is detected the home screen displays a pop-up window 429 that can overlay the home screen and notify the user that one or more possible meals were detected and optionally give the time when each of those meals were detected. Pop-up window 429 includes a selectable field where the user can choose to log a meal for each time period corresponding to the detected excursion or event, and can also include a selectable field where the user can choose to ignore the notification of window 429. Here, screen 428 includes a historical graphical display 406 of the user's analyte level with indicators 408 for each detected glucose excursion or meal event. When pop-up screen 429 is displayed, the corresponding detected events where meal information has not yet been entered can be graphically identified or distinguished from those events where meal information has already been entered or where it is not required.

In an alternative embodiment, upon detection of a glucose excursion or meal event, the meal monitor application can initiate or display screen 430 of FIG. 4D to identify the detected event to the user (at least in part by way of indicator 408) and prompt the user to enter a meal information by selectable Event Detected button or field 412. Alternatively, the meal monitor application can display the Event Detected button 412 on another screen currently being displayed to the user. The Event Detected button 412 can be alternatively be labeled as a Meal Detected button.

Selection of the option to log the meal in pop up screen 429 or selection of the Event Detected button 412 can cause the meal monitor application to transition to screen 420 of FIG. 4B, reproduced again as FIG. 4E for ease of illustration. There, as in the example embodiments described with respect to FIGS. 4A and 4B, the user can enter meal information photographically via button 422 and/or textually via free text field 424, and save that information via button 426. Because detection of the meal event occurs after consumption of the meal, the user may choose to photograph packaging for the meal, or scan a barcode of the meal packaging, instead of photographing the meal itself. All variations to the meal information entry process described with respect to FIGS. 4A and 4B (including, but not limited to the pick list and drop-down list variations), including all variations to the meal information entry process described herein but not shown in FIGS. 4A and 4B can likewise be applied here.

When a user logs a meal at his or her own discretion, for example using screen 420 of FIG. 4B, the meal monitor application can require the user to describe the time at which the meal occurred in any of the formats described herein. When the meal monitor application detects an event, then the application already has access to time information about the event. Thus, when the user is prompted to enter information about the meal event such as, for example, using screen 430 to access screen 420, that determined time information can be displayed to the user so that the user has an option to edit the time information if not accurate. If a rise in the analyte data is used to detect a meal event, then the time at which the rise episode starts can be the default displayed meal time, with compensation for sensor and digestive-based lags as described herein.

In some example embodiments, the data entry process is streamlined to further minimize the burden on the user when inputting data. The lower the burden the more likely the user is to utilize the meal monitor application, and thus enjoy its benefits. In one example embodiment, the meal monitor application can be configured so that it does not actively prompt the user for any nutritional information about the meal nor the meal type (e.g., breakfast, lunch, or dinner) when accepting a log entry from the user (e.g., step 302 of method 300) and/or when accepting information from the user in response to a prompt for meal information (e.g., step 310 of method 300). In another example embodiment, the meal monitor application is configured so that it only accepts an image of the meal and/or a free textual description of the meal and does not permit any other information about the meal to be entered when accepting a log entry from the user and/or when accepting information from the user in response to the prompt.

Referring back to FIG. 3A, once the information for a meal event has been entered at 312, the meal monitor application will associate the analyte data with that meal information in memory at 314. Specifically, the analyte data occurring around the time of the meal event can be associated with the information for that meal event. The analyte data selected to be associated with the meal event can be chosen based on the time during which the meal event occurred and optionally a period of time after which the meal event occurred to reflect changes in the analyte level due to digestion of the meal.

In some embodiments, analyte data occurring from the time at which the meal began until a period of time after the meal ceased can be associated with the meal event. Also, analyte data occurring from the time at which the meal began until the conclusion of a detected glucose excursion can be associated with the meal event. In some embodiments, analyte data collected during a fixed range of time around the meal event is associated with the meal event, for example, any combination of from one, two, or three hours before the meal event (e.g., as measured by initiation of the meal event, a median time of the meal event, or a conclusion of the meal event) until one, two, three, four, five, six, seven or eight hours after the meal event. In each case, times over which the meal event occurred can be identified based on information entered by the user or can be identified algorithmically through analysis of the analyte data.

Data collected from analyte sensor 104 may temporally lag the user's actual blood glucose level, for example if sensor 104 is sensing data from within the user's interstitial fluid, and to a lesser degree, dermal fluid. Thus, correlation of analyte data to meal consumption times should take into account this sensor-based lag, which may typically be on the order of 3 to 20 minutes depending on fluid type and sensor placement. This lag is in addition to lag time that results from absorption of food through the digestive process. In other words, there is a time delay between the time when food is consumed and the time when the results of that consumption are reflected in the user's blood glucose level. Thus, in some embodiments, the analyte data associated with the meal event is selected as described above with additional compensation for digestive lag and/or sensor-based lag. For example, the first analyte data points to be associated with a meal event may be based on the commencement of that meal event, but delayed by 10 minutes (five minutes to compensate for digestive lag plus five minutes to compensate for sensor-based lag).

The association of analyte data with a meal event can be used in determining a glycemic impact of the meal event at 316. In some embodiments, determination of the glycemic impact of the meal event can be done algorithmically with reference to analyte data contemporaneous with the meal event, and this algorithmic processing can constitute both steps 314 and 316. The determined glycemic impact can be determined quantitatively in terms of maximum (peak) or minimum glucose level, median or mean glucose level, minimum-to-maximum change in glucose level (delta (A) glucose value), percent variability of glucose level, duration of glucose response, rate of change of glucose level, area of the glucose response, and any combination thereof.

The meal event detector outputs information about the glycemic response to the meal that can be used to characterize the magnitude or severity of the response. For example, the meal event detector can output the start time and the peak time for each detected meal event. The meal-start glucose can be the glucose value at the meal event start time and the peak glucose can be the glucose value when a rise episode of the detected meal event peaks. The difference in these glucose values can be determined to provide a delta glucose measure of the glycemic response to the meal.

In other embodiments, the "area" of the glycemic response is determined in terms of glucose and time; for instance, a sum or integration of each glucose reading is determined from the meal start time to either a) the next meal start time, or b) when the glucose readings fall within a threshold value of the meal start glucose value (e.g., within 10 mg/dL), as it can be difficult to accurately assess where the glycemic response ends. This sum or integration value is proportional to the glucose multiplied by time area of the glucose response. Each of the metrics described herein, as well as others, can be used as the basis upon which to rank and/or sort the glycemic response to meals output to the user as described below.

Another problem that specifically arises from the use of a meal monitoring and detection software is that in some instances multiple meal events may be detected and/or logged in close temporal proximity to each other. This problem can result in the identification of too many meal events when, from the user's perspective, the events were part of the same meal.

In these cases, the meal monitor application can cluster or group the meal events into one meal cluster. For example, meal events logged or detected within a time range condition (e.g., one hour, 90 minutes, etc.) of each other can be merged into one meal cluster. The meal monitor application can then analyze and output glycemic response data to the user describing the meal cluster as a whole as opposed to each separate event therein, which is intended to correspond to the user's concept of a meal (e.g., dinner may be one cluster of different courses). Thus, each meal event or meal cluster that is analyzed and displayed to the user is separated by at least the value of the time range condition, which can result in a more natural information output that is easier to comprehend. To facilitate this, the meal monitor application can avoid placing a restriction on the number of meal events considered per day.

Figure 3D:
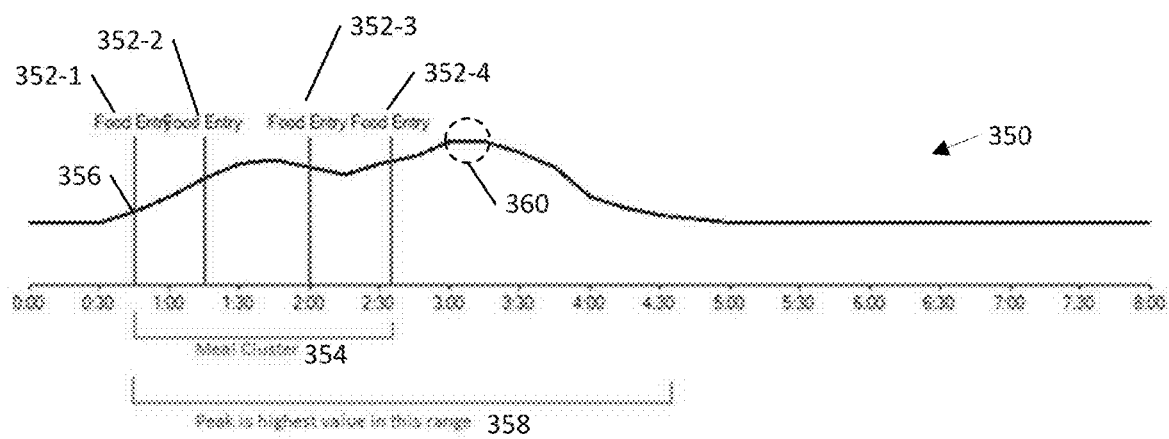
FIG. 3D is an example of a graph of analyte data over time displaying an example set of data with four different meal events.

FIG. 3D is an annotated graph 350 of analyte data over time displaying an example set of data where four different meal events (352-1, 352-1, 352-3, and 352-4) have been automatically detected or manually logged. These four different meal events are considered a single meal cluster 354 because each event 352 is within a time range condition, which can be a predetermined factory-set condition or a condition set by the user. In this example, the time range condition is one hour, and all four events 352 are grouped together because each individual event 352 is within one hour of at least one other event 352.

In some embodiments, a maximum time limit can be placed on the length of time from a first event 352 that the meal monitor application will consider other events for clustering. For example, the time range condition can be one hour with a meal cluster maximum length (not shown) of 90 minutes after the first event 352-1, in which case meal events 352-1, 352-2, and 352-3 would be grouped as one meal cluster and meal event 352-4 would be considered a separate meal event from the cluster.

As described herein, the time of the meal event can be the time input by the user in the manual logging process, the time at which an analyte episode corresponding to the meal event is first detected (e.g., the start of a rise), the time at which an analyte episode corresponding to the meal event is first detected plus the addition of a delay (e.g., 15 minutes, 25 minutes), the mean or median time determined from the duration of the analyte episode (e.g., the meantime from start to end of a rise or the time of the median data measurement collected during the rise), or any other desired time.

In some embodiments, multiple different meal events detectors, based upon different algorithms, can be used. Each individual meal event detector routine can be independently run on the collected analyte data to identify detected meal events and/or their start times. The meal monitor application can then choose which results to use for analysis and display to the user. For example, if each meal event detector outputs a different start time for the same meal event, then the meal monitor application can average the two and use the averaged meal start time for analysis and display. In another example, the meal monitor application may consider an event to be detected only if each meal event detector actually detects it. In yet another example, the meal monitor application may consider an event to be detected if at least one meal event detector actually detects it.

In the example depicted in FIG. 3D, a pre-meal or meal-start glucose value 356 can be the glucose value at the start of the first meal event 352-1 of meal cluster 354. If necessary, this value can be obtained from the data measurement occurring closest in time before or after the time of meal event 352-1. If no data measurement is present within a maximum time range, such as 30 minutes, then the meal monitor application may consider the pre-meal glucose value to be unknown.

A meal peak glucose value can be the highest glucose value occurring in the analyte data collected during or after meal cluster 354. Meal peak glucose time range 358 denotes an example time range window that is searched for the occurrence of the highest glucose value. Time range 358 can start it the time of the first meal event 352-1 and can end at the time of the last meal event 352-4, or more likely, can and the predetermined time after the last meal event 352-4. In the embodiment depicted in FIG. 3D, time range 358 begins at the time of the first meal event 352-1 and ends two hours after the last meal event 352-4. Thus, the meal peak glucose value would be the magnitude of values in region 360 where the analyte data peaks and maintains a constant level. If no readings are present in window 358 the meal peak glucose value can be considered as unknown.

A meal delta glucose value can be determined by subtracting the pre-meal glucose value from the meal peak glucose value. If one of or both of those values are unknown, then the meal delta glucose value can be considered as unknown.

Referring back to FIG. 3A, the determined glycemic response or impact can then be output to the user at 318, such as visually on a display of the smartphone, as will be described below with respect to FIGS. 5A-F. In many embodiments, this is done immediately with a presentation of information about the corresponding meal event so that the user can immediately understand the impact of a particular meal on the user's analyte levels, making the application compelling to use. The determined glycemic response can be output in quantitative and/or qualitative terms. For example, the determined glycemic response can be output in the same quantitative measure in which it was determined at 316. This can be done in text and/or graphical form. Also, the determined glycemic response can be output qualitatively, for example, described in text as low or minor, moderate or medium, or high or severe, or any synonym thereof. Less or more graduations of magnitude can be used as well. The determined glycemic response can also or alternatively be output as an icon or other imagery (e.g., colored shapes of various degrees of magnitude).

System 100 can also (or alternatively) issue a medication or other treatment output at 320. In certain embodiments the output can inform an individual, such as the user or a medical professional, that medication (e.g., insulin) or treatment may be warranted, for example, due to the risk or occurrence of a high glucose excursion or hyperglycemia. This notification can be a visual and/or audible notification output by reader device 120.

An output issued at 320 can supply information directly to the user's medication or treatment program on the same device or a different device in communication with the device executing the meal monitor application. This information can be used by the treatment program in determining whether a modification to a user's treatment profile (e.g., a basal insulin delivery schedule or a bolus dose) is warranted or to prompt the user as to whether a change to the user's treatment profile should be implemented.

An output issued at 320 can cause the user's drug delivery device 160 to administer medication to treaty a potential or actual high glucose condition, such as by administration of a bolus dose or by a modification to a basal dosage profile or schedule. This can be done with the user's approval, such as in a semi-closed loop, or automatically without the user's approval, such as with a true closed loop or artificial pancreas.

The meal monitor application can also issue any of the aforementioned medication or treatment outputs when a user indicates that a meal is or was recently consumed where that meal has previously caused a glucose excursion, such as a rapid rise or high glucose level. In this manner system 100 can pro-actively treat the anticipated glucose change without waiting for the detection of the actual change with sensor 104.

Outputting information from the meal monitor application to a medication or treatment program and/or drug delivery device enhances the ability of the program or device to implement accurate therapy for the user. More accurate information about the user's meal history is captured and made available to the program or device to make the appropriate, sometimes subtle, adjustments to the user's treatment. This can, in turn, reduce the occurrence of errors in medication administration (e.g., over or under-dosing), which constitutes an improvement to the functioning of electronic and mechanical systems with drug delivery capability.

FIGS. 5A-F depict example embodiments of GUI screens that can display output information to the user or any other individual in step 318 of method 300 (see FIG. 3A) or at other times during use of the meal monitor application. These screens can be displayed on any of the embodiments of reader device 120, drug delivery device 160, or local computer system 170 described herein.

FIG. 5A depicts screen 502, which includes a series, listing, or group 500 of logged meals 505-1 through 505-N. Group 500 is generally referred to herein as a ranking report 500. Ranking report 500 shows all or a subset of meal events 505 (and activity, if applicable) for which data has been collected. If a meal cluster was identified, then the meal events within the cluster are grouped together and displayed as one meal event 505. The ranking of events 505 can be ordered by the magnitude of the glycemic response. When presented to the user, ranking report 500 can display starting at the top of the list, showing the meals 505 that resulted in the largest glycemic responses first, followed by those that resulted in glycemic responses of decreasing magnitude.

In another embodiment, ranking report 500 can display the most recent meal causing a glucose excursion and the user can scroll (upwards or downwards) through the list which is again sorted in order of highest to lowest glucose excursion magnitudes. In yet another embodiment, ranking report 500 can display the meals causing glucose excursions in order of most recent to least recent. Toggle sort buttons can be provided that allow the user to change the criteria upon which the ranking in report 500 is determined (e.g., change ranking by meal type, date and time, glucose excursion magnitude, and the like).

In the embodiment depicted in FIG. 5A, for each meal 505 within ranking report 500, an image of the meal can be displayed if available, along with the date and time at which the meal was consumed, along with an indication of the magnitude of glucose response, which can be presented in any of the output forms described herein. Instead of or in addition to an image, the name of each meal 505 can be described textually. In addition to ranking meals by their glycemic response, ranking report 500 can rank occurrences of a single particular meal type by their glycemic response. For example, portion sizes, times of day, and glycemic response for a commonly consumed spaghetti dinner can be ranked and displayed.

If a glucose excursion occurred but no meal information was entered, then the time, date, and magnitude of the glucose excursion can be displayed in report 500 along with a selectable button or field which, upon selection, will prompt the user to enter information about the meal, such as by displaying screen 420 of FIG. 4B. If there is meal information but no photo, then an missing photo indicator can be displayed so that the date and/or time is aligned with the other entries in report 500.

If meal event detection sensitivity settings or glucose excursion sensitivity settings are adjusted during the use of the meal monitor application, then the data displayed in ranking report 500 can be retroactively adjusted so that all data is displayed with one common array of sensitivity settings. Thus, each time the user displays a ranking report 500 or otherwise displays historical meal or analyte information, the meal monitor application can recalculate the displayed information to retroactively compensate for sensitivity adjustments.

Selecting or clicking on a meal in ranking report 500 can initiate a screen with additional information about that particular meal. FIG. 5B depicts an example embodiment of such a screen 512 that can include a graphical display 514 of historic glucose (e.g., 8 hours, 24 hours, 48 hours, or other) surrounding the meal event. Graphical display 514 can include any increment of time prior to, after, and surrounding the meal. In one example embodiment, graphical display 514 is an eight hour period of time with two hours of data prior to the start of the meal event and six hours of data after the start of the meal event. Graphical display 514 can also include time periods of any of the various ranges of analyte data associated with the meal event at 314 of method 300 (see the description with respect to FIG. 3A).

An excursion indicator 408, in this case a shaded area under a glucose curve, can be displayed for each excursion detected in the analyte data of graphical display 514. The occurrence of the selected meal event along with every other meal event within the period of time of graphical display 514 can be indicated by a food icon 516, a photo of the meal, and/or text describing the meal. Alternatively, meal events that are clustered together can be indicated as only one event. Selection of a particular meal event can cause another screen 512 to display, which is instead focused on that newly selected meal event. Alternatively, selection of a meal event can cause a pop up window to display with information about that particular meal event.

In another embodiment, selecting an individual meal from screen 502 of FIG. 5A can display an embodiment of screen 512 that includes graphical display 514 along with an image of the selected meal, with a summary of the meal contents of that meal (e.g. portion type, portion size, etc.) and/or any free text entered by the user with respect to that meal. Thus, all or most of the information entered by the user to describe the meal is displayed, along with historical analyte data around that meal event.

In another embodiment, each meal displayed either in the ranking report or elsewhere may be displayed with the associated glucose trace. When displayed with other meals on the ranking report, the user can compare features of different meals, such as the relative peak glucose time and how long the glucose response lasts. The display may highlight some of these features, such as displaying the numeric elapsed time of the peak glucose relative to the start of the meal.

FIG. 5C depicts an example embodiment of a screen 520 showing an organizational layout of information for display to the user about a particular meal, for example such as would be displayed upon selecting a particular meal from ranking report 500. The date where a time corresponding to the meal event first occurs is displayed in region 522, followed by the time (or time range if supplied) of the meal event. Beneath one or more images 524 of the meal can be displayed, for example, if the user captured a photo of each course of the meal. Meal peak and meal delta glucose values can be displayed to the right at 526, along with any free textual description of the meal at 528.

FIG. 5D depicts an example embodiment of a screen 530 populated with example information about a particular meal. Screen 530 is similar to screen 520 but also includes indications of detected meal events 532-1 and 532-2 for which no information is yet been entered, e.g., a missed entry. Each meal event 532 is followed by a user selectable log buttons 533-1 and 533-2 for logging information about the meal event and user selectable ignore buttons 534-1 and 534-2 for selection if the user chooses not to enter information about the meal or if no meal in fact occurred. If the user chooses to log information about the meal, then a log information screen such as screen 420 of FIG. 4E can be displayed with the meal time pre-populated as the time of the missed entry. If the user returns to screen 530, the information should be recalculated to account for the newly logged data. If the user chooses to ignore the missed entry then a log of missed entries can be updated and that ignored entry can be removed from screen 530.

Figure 5E:
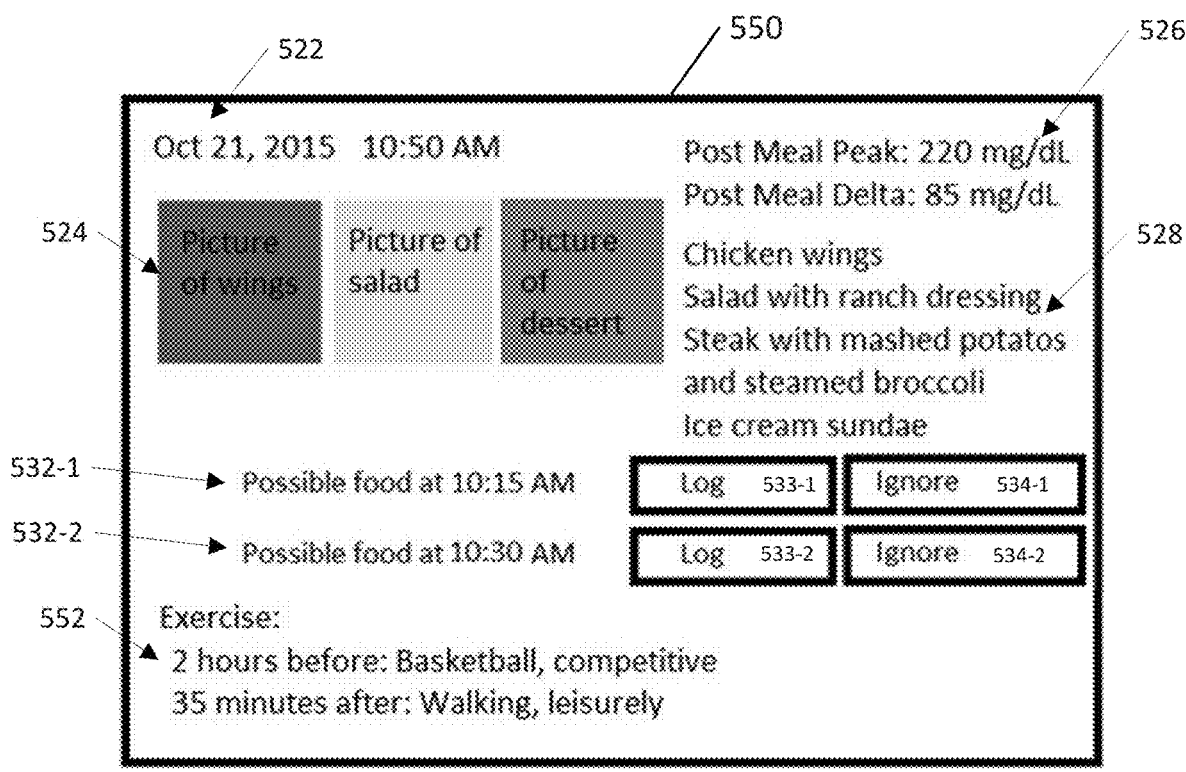

FIG. 5E depicts an example embodiment of a screen 540 similar to screens 520 and 530. Here, screen 540 includes six photographs of a meal cluster occurring between 10:50 am and 11:20 am. In any of the embodiments described herein, selection of a particular photograph can cause the display of a pop up window containing a larger display of that image.

Figure 5F:
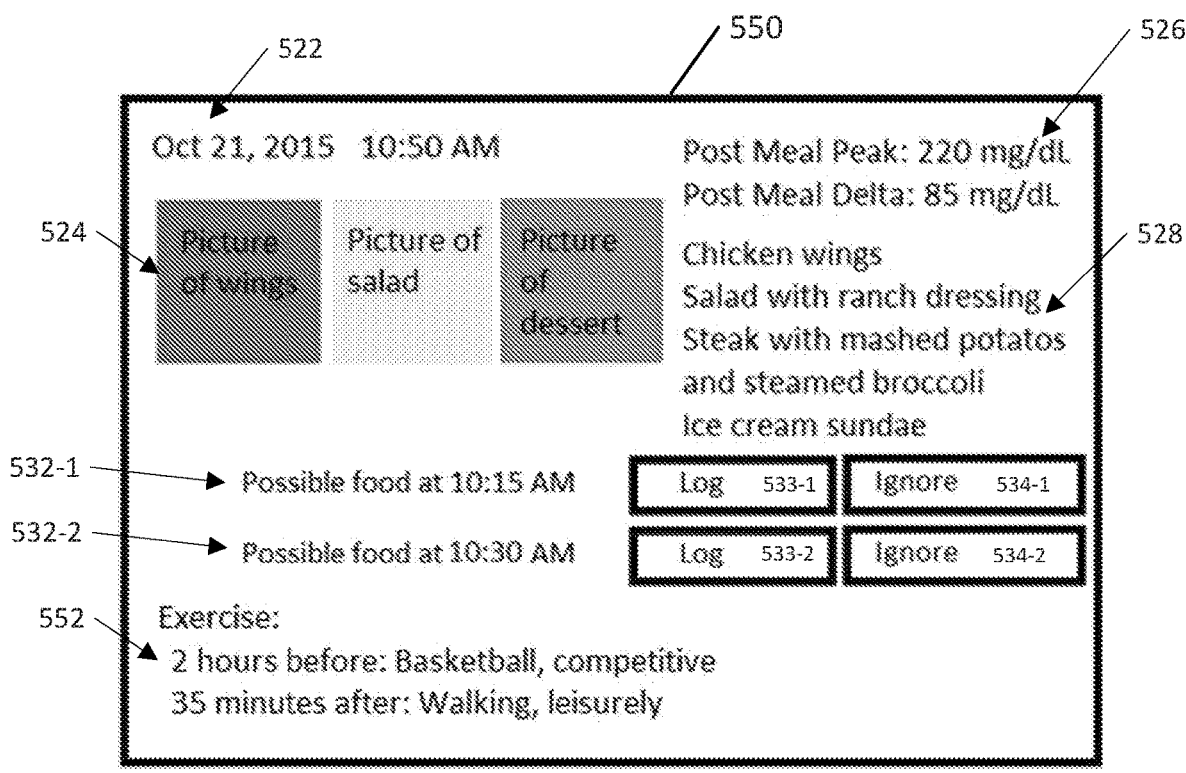

FIG. 5F depicts an example embodiment of screen 550 similar to the previous screens but with an indication of logged or detected exercise or other activity 552 and the times at which that activity occurred in relation to the meal event described in screen 550.

Referring back to FIG. 3A, method 300 can repeat itself such that the meal monitor application continues to receive, monitor and store the analyte data (e.g., step 304 of method 300) and search for detected events 306 indefinitely. The recently entered information about a detected or logged meal can be included in the options presented to the user for entering meal information each time a new event is detected.

The meal monitor application can be used with software that monitors and collects information about the user's activity level. Thus, for each of the embodiments described herein that relate to the logging of meals, prompting for information about meals, associating analyte data with meals, determining glycemic impact of meals, and/or outputting information about the relationship between a meal and the user's glucose level, it should be understood that those embodiments can likewise be applied to an activity performed by the user that is not the consumption of the meal. Common examples of such activities are exercise, work, and rest. All such activity related embodiments are within the scope of this disclosure. To assist in the collection of activity data, each sensor control device 102 can include or otherwise be configured to operate with an activity monitor that continually or repeatedly measures the level of activity for each wearer (e.g., calories burned per time of day) and/or a heart rate monitor that monitors and enables the recording, by system 100, of the wearer's heart rate. Additional example embodiments of analyte monitoring systems that include or operate with activity monitors and heart rate monitors are described in the U.S. Provisional Patent Application titled "System, Device and Method of Dynamic Glucose Profile Response to Physiological Parameters," filed on the same date as the present application, and attached hereto as appendix A. The embodiments described in appendix A can each be used with any and all embodiments described herein for any and all purposes.

The information output by the meal monitor application, such as ranking report 500, provides the user with concrete and immediate information regarding the impact of their meals on their glucose levels. This output information can help users learn to avoid or minimize certain meals in their diet that they did not realize were impacting their glucose levels, e.g., that they did not realize were driving their glucose levels so high. This output information can also help users learn to control the portion sizes of their meals by seeing the relative impact of different portion sizes on their glucose levels.

The meal monitor application can also encourage the individual to experiment with different meals, times, components, and can be compelling and fun to use. This meal monitor application promotes the use of analyte sensors by a large demographic including people with Type-Two diabetes, pre-diabetes, metabolic syndrome and people without diabetes—basically any person who is motivated to improve their health by changing their diet and/or activity habits.

The meal and/or activity monitoring applications described herein can have substantial benefits for individuals that are newly diagnosed with Type-Two diabetes or pre-diabetes. Often, when an individual is confronted with starting diabetes medication, they are highly motivated to try diet and exercise modifications in order to avoid or delay the need for medication.

Thus, a clinical scenario for use of various systems and software disclosed herein is for individuals that are newly diagnosed, for example, based on a fasting glucose test and/or an A1c test, to follow up by wearing a sensor control device 102 that interfaces with a reader device 120 that can be blinded so that the user's current and historical analyte levels are stored but not shown to the user. The user wears sensor control device 102 for a period of time, e.g. two weeks, after which the analyte data is collected by a medical professional and the analyte patterns are revealed to the user. This blinded usage minimizes the impact of the system on the user's habits and tendencies, and thus gives the medical professional a better understanding of the specific glycemic issues and how best to address them with medication. At this point the physician can give the individual the option to try to address their diabetic condition with diet and exercise using the software applications described herein, in conjunction with nutritional training and an exercise plan. This may be followed up with another sensor control device 102 and reader device 120 to allow the medical professional to evaluate progress, and to determine if medication or further diet/exercise intervention is still required.

Additional metrics and reports geared towards the medical professional can be included. For example, a study on 14 normal glucose tolerance (NGT), 12 impaired glucose tolerance (IGT), and 16 non-insulin dependent diabetes mellitus (NIDDM) individuals showed that the first phase insulin response to an intravenous glucose challenge is absent in Type-Two diabetes mellitus (T2DM) subjects. With sufficient monitoring of meal information paired with glucose excursion tracking, changes in the first phase insulin response can be tracked by the medical professional.

Moreover, a quarter of the world's adults have metabolic syndrome. These adults have a five-fold higher risk of developing Type-Two diabetes. In addition, evidence indicates that most of the damage to a person's beta cells is done prior to pre-diabetes diagnosis, demonstrating the need for intervention prior to diagnosis. Since progression to Type-Two diabetes starts from impaired glucose tolerance (IGT) well before impaired fasting glucose (IFG), sensor-based hyperglycemia and post meal excursion based metrics that have been shown to reliably predict the onset of or diagnose Type-One diabetes may be adaptable for those with metabolic syndrome. Thus, the software applications and systems described herein for newly diagnosed diabetes individuals is therefore applicable to the metabolic syndrome population.

Furthermore, the software applications and systems described herein have applicability to those wishing to lose weight, as a general correlation between glucose excursions and weight gain is known.

To the extent information is input by a user, device, or other software, then that information can be received, read, and if containing an instruction, implemented by the processing circuitry (which can be a single processor or distributed across multiple processors or devices having processing capability). Those instructions can be stored in a memory of, and executed by processing circuitry of, any and all embodiments of a reader device, drug delivery device, meter, computer system, or other computing device described herein.

Embodiments of Analyte Monitoring a Population for Meal and Activity Planning

Also provided herein are example embodiments that enable analyte monitoring for a local collective, population, community, or group of users. Data collected from the monitoring of this population can be used for a number of purposes, including providing guidance and meal and activity planning. These embodiments will be described with respect to one example application, namely, use of population monitoring at a senior care residence facility or home. However, these embodiments are not limited to this example application and numerous other such applications exist and are within the scope of this disclosure. The population monitoring embodiment can be used alone or in combination with the meal evaluation and planning embodiments also described herein.

In senior residence facilities meals are prepared and served by the residence facility staff. Residence populations may be susceptible to diabetes or pre-diabetes due to age related decrease in insulin response, decrease in physical activity, weight gain, and/or other factors. Generally speaking, the residents form a population and each member of the population can wear an in vivo sensor 104, such as with sensor control device 102. Analyte data collected by each member's sensor control device 102 can be automatically read by a reader device while the members are within range of the reader device, for example, when all or most members of the population are in the same general proximity to each other within a common area (e.g., a dining room, etc.) during a meal time (e.g., breakfast, lunch, or a dinner time). Alternatively, the data can be read from each member of the population at different times with respect to each other.

Figure 6A:
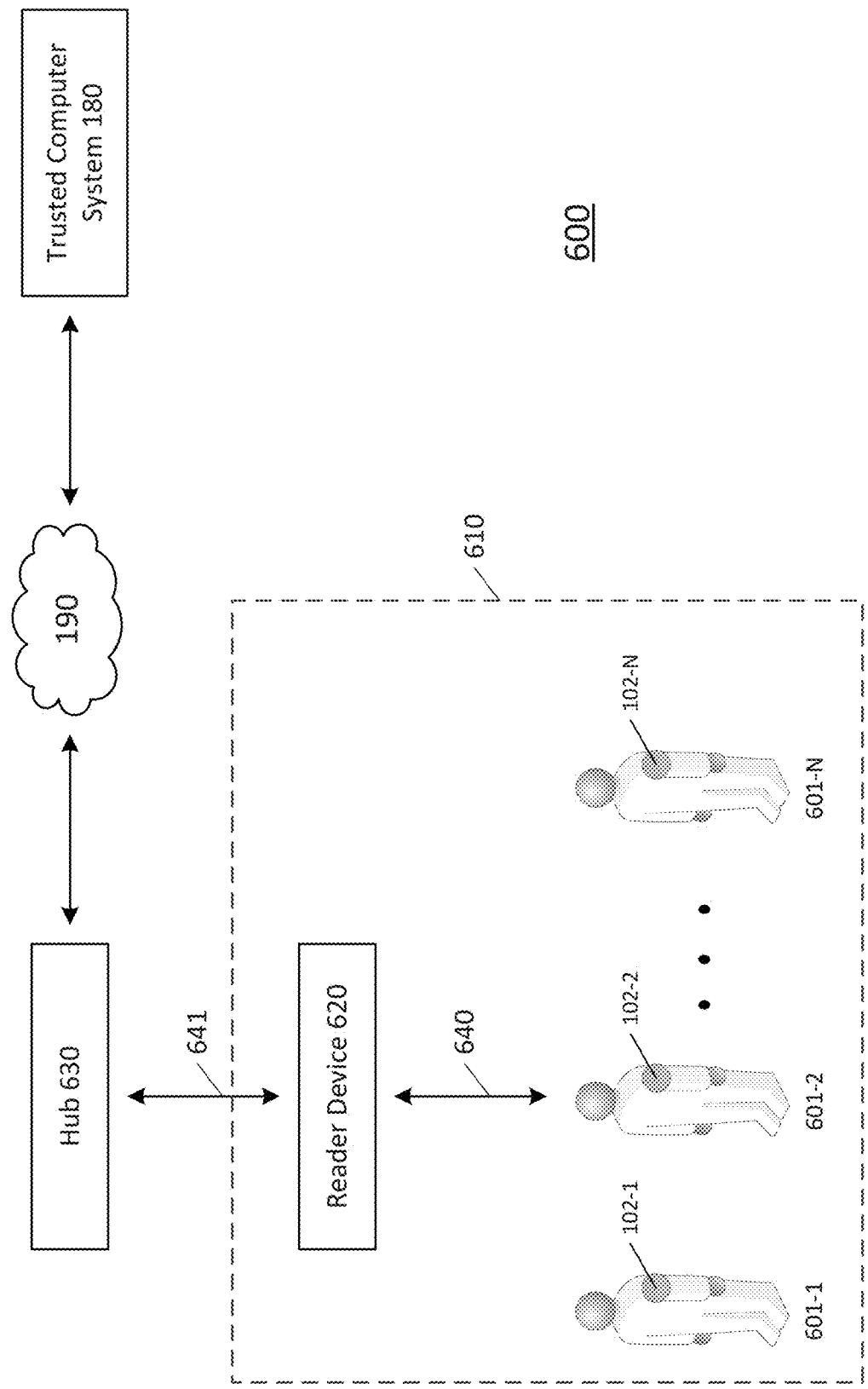
FIG. 6A is a block diagram depicting an example embodiment of an analyte monitoring system for use with multiple individuals in a local population.

FIG. 6A is a block diagram depicting an example embodiment of using an analyte monitoring system 600 to collect analyte data from N members of a population. Here, system 600 includes a reader device 620 capable of communicating with a plurality of sensor control devices 102-1 through 102-N, located on a plurality of device wearers 601-1 through 601-N, respectively. N can be any desired number. Reader device wearers 601 are physically located in a common area 610, such as a dining room.

Reader device 620 can be configured in a manner similar to all of the embodiments of reader device 120 described herein, but also with the capability to communicate with each of the plurality of sensor control devices 102 simultaneously, sequentially, or at scheduled or random intervals (e.g., as the wearers 601 cycle through the common area through the course of a day). This communication can occur over a wireless or wired communication path 640, which can be configured similarly to the wireless communication path 140 described with respect to FIG. 1. For example, any of the wireless communication protocols described herein can be used, and this communication path can be unidirectional or bidirectional.

In one example embodiment, reader device 620 pairs with each sensor control device 102 using a Bluetooth or Bluetooth Low Energy communication protocol. Reader device 620 can collect analyte data from each wearer 601 and store the data locally and/or upload the data to another computer system, such as a remote internet server. Here, reader device 620 is adapted to communicate with a wireless hub 630, which in turn can communicate data to a trusted computer system 180 over network 190, through any number of intervening servers. The communication link (or path) 641 between reader device 620 and wireless hub 630 can operate according to any desired wireless protocol. In this embodiment, wireless hub 630 is a Wi-Fi hub and link 640 is a Wi-Fi connection. Thus, reader device 620 can function as a Bluetooth to Wi-Fi bridge.

In other embodiments, reader device 120 can include the electronic circuitry hardware and software that permits reader device 620 to upload data directly to trusted computer system 180 over network 190 such that Wi-Fi hub 630 can be omitted. For example, reader device 620 can include mobile telephony functionality, satellite communication functionality, a cable modem, Ethernet functionality, and so forth.

In many embodiments trusted computer system 180 can be local to the residence population 601-1 through 601-N such that communication over network 190 is not necessary. For example, reader device 620 can upload the collected data over communication link 641 to Wi-Fi hub 630, which can then pass the information directly to trusted computer system 180 over a local wired or wireless connection, or reader device 620 can upload the collected data directly to trusted computer system 180 over a local wired or wireless connection.

Reader device 620 can also perform any amount of desired processing on the analyte data collected from sensor control devices 102. For example, reader device 620 can simply pass through raw data collected from each sensor control device 102 to trusted computer system 180 by way of wireless hub 630 and network 190. In another example, reader device 620 can algorithmically process the collected raw data and determine the analyte level of each wearer 102, and then upload that processed information to trusted computer system 180.

Reader device 620 can be programmed to automatically recognize and pair with each sensor control device 102 within its communication range. However, greater selectivity may be desired to allow data from only particular sensor control devices 102 to be collected. In such embodiments, reader device 620 can be programmed to recognize and pair with only a subset of sensor control devices 102. For example, sensor control devices 102 can include a dedicated identification flag or code that is transmitted to reader device 620 during a data collection or pairing procedure. Reader device 620 can be programmed to upload data from only those sensor control devices 102 that transmit this flag or code.

In another example, reader device 620 itself, or a different reader device 120, can perform a recognition procedure on each sensor control device 102 that reads an identification number (e.g., a serial number) of that sensor control device 102 and associates that identification number with the subset of sensor control devices 102 that will communicate with reader device 620. During this recognition procedure, the name or identification of the wearer 601 of each sensor control device 102 can be associated with that device identification number such that data collected from each sensor control device 102 can be linked to a particular wearer 601. If reader device 620 is used for this recognition procedure, then the list of sensor identification numbers can be stored locally in the non-transitory memory of reader device 620. If a separate reader device 120 is used in the recognition procedure than the list of sensor identification numbers can be uploaded to trusted computer system 180 and then communicated to reader device 620.

In order to permit communication with as many sensor control devices 102 as possible, reader device 620 can be positioned centrally within the common area 610. For example, reader device 620 can be mounted overhead in the center of the room or, in the case of a dining room, can be positioned on the dining table. In some embodiments, multiple reader devices 620 can be used, for example one reader device 620 on each table, to increase the overall communication area.

Each sensor control device 102 can include enough non-transitory memory to store analyte data for the entire time period between readings by reader device 620. This allows reader device 620 to collect all or substantially all of the analyte data of each wearer 601 throughout the course of a day or week. For example, sensor control device 102 can include 12 hours of memory to record analyte data overnight from after a dinner meal until a breakfast meal. Other memory sizes corresponding to different lengths of time can also be used (e.g., 8 hours, 24 hours, 72 hours, etc.).

Although these embodiments are described with respect to use of a common reader device 820 for the local population, is also the case that each member of the local population can use his or her own reader device 120 to collect the analyte data. In such cases, each reader device 120 could communicate directly to trusted computer system 180 or to a data collection hub that in turn uploads the data to the appropriate computer system.

Figure 6B:
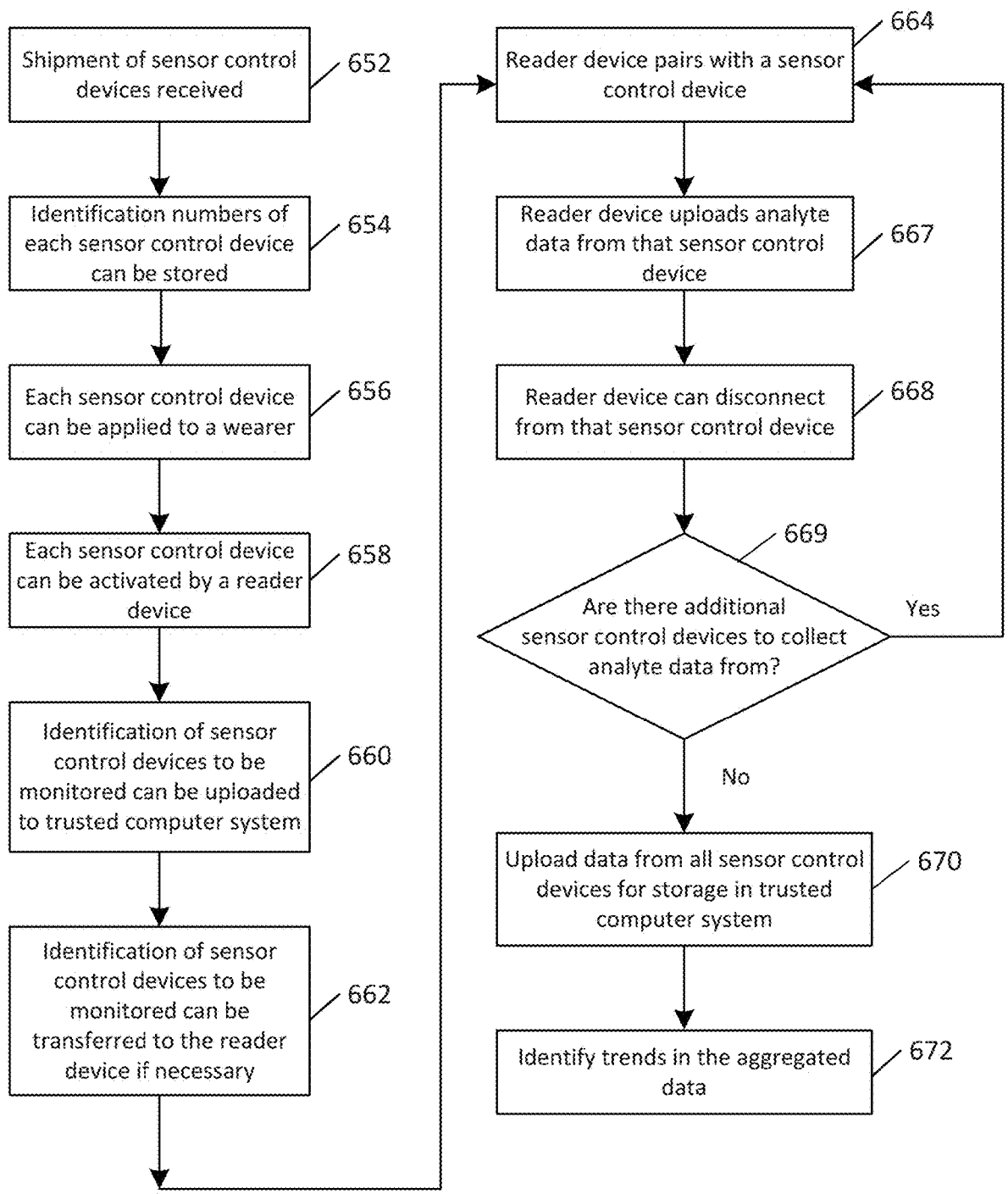
FIG. 6B is a flow diagram depicting an example embodiment of a method of using an analyte monitoring system with multiple individuals in a local population.

FIG. 6B is a flow diagram depicting an example embodiment of a method 650 of analyte monitoring a population for meal and/or activity planning. Like the system 600 of FIG. 6A, method 650 is described with respect to the collection of data from residents of a senior care facility during mealtime.

A shipment of sensor control devices 102 is first received by the facility at 652. Facility personnel can optionally upload the identification numbers of each sensor control device 102 to trusted computer system 180 at 654. Each wearer 601 to be monitored can then apply a sensor control device 102 such that the analyte sensor is positioned in vivo and ready to sense analyte data at 656.

Each applied sensor control device 102 can then be initialized, activated, or recognized at 658 by reader device 620 or another reader device 120, as previously described, to identify the subset of sensor control devices 102 that will be sending data to reader device 620. This recognition procedure can be performed by each wearer 601 or a member of the facility personnel and can optionally include associating the wearer's name or identification with his or her sensor control device 102. This data can be uploaded to trusted computer system 180 at 660, which can in turn communicate the list of sensor control devices 102 (and optionally the associated wearers 601) to reader device 620 at 662.

Reader device 620 can monitor for the presence of sensor control devices 102 within common area 610 and then pair with each sensor control device 102 of the subset as those sensor control devices 102 are discovered in common area 610 at 664. If common area 610 is the dining hall, then many sensor control devices 102 will likely be discovered in a short time span. After establishing a connection with a particular recognized sensor control device 102, reader device 620 can read or upload the analyte data stored within that sensor control device 102 at 667, which may represent a series of analyte level measurements of the wearer 601 since device 102 was last read or the entire history of analyte level measurements stored in the memory of device 102 (in which case measurements overlapping those already collected can be ignored). After collection of the analyte data, reader device 620 can disconnect from that sensor control device 120 at 668 and, if reader device 620 determines that another sensor control device 120 is present and needs to be read at 669, then proceed to pair with and collect analyte data from the next recognized sensor control device 120 (back to 664).

This process is repeated until analyte data has been collected from all recognized sensor control devices 102 within range of reader device 620. Reader device 620 can continually monitor for sensor control devices 102 throughout the course of the day as meal schedules for particular residents may vary and accordingly their presence within common area 610 may not be predictable. Reader device 620 can be programmed with a waiting period so that, after data from a particular wearer 601 is collected, reader device 620 will not attempt to pair with that wearer's sensor control device 102 again until sufficient time has passed. For example, if the wearer briefly leaves common area 610 then reader device 620 will not attempt to collect data again upon reentry. This waiting period may be, for example, 30 minutes, one hour, 90 minutes, and so forth. The next time reader device 620 recognizes sensor control device 102 after expiration of this waiting period, reader device 620 will begin the data collection procedure again. Thus the process can repeat continually.

Data from all of the sensor control devices 102 can be stored in non-transitory memory of trusted computer system 180 at 670 and the aggregated data can be examined or processed to identify trends among the resident facility population at 672. An example set of aggregated data is depicted in human readable form in FIG. 7. Here, the x-axis represents time and the y-axis represents analyte concentration, although each axis can be different metrics as well. Each point (X) in the distribution represents an analyte concentration reading collected by reader device 620 from a particular sensor control device 102. Thus the distribution includes readings from the same wearer 601 at different times as well as readings from different wearers 601 (also at different times). Further, the aggregated data can include readings collected from each wearer on different days, for example, to allow identification of trends that are independent of a single meal occurrence.

Menu information, such as meal contents (e.g., caloric content, carbohydrate content, sugar content, protein content, and the like), meal time of day, and meal type (e.g., breakfast, lunch, snack, or dinner) can also be provided to trusted computer system 180 and linked to the aggregate data so that correlations between analyte data and meal information can be identified. Meal events can be detected in the aggregate data using any of the meal event detectors described herein, or by analysis of predefined time periods for each day on the assumption that schedule meals are provided. The analyte pattern of the resident population after the previous meal can be compared against the meal information to identify factors causing undesirable analyte events, and the meals can be adjusted to minimize these events. Even if particular excursions are not occurring, meal contents, type, and times, can be adjusted to provide maximum stability or analyte levels across the resident facility population.

Figure 7:
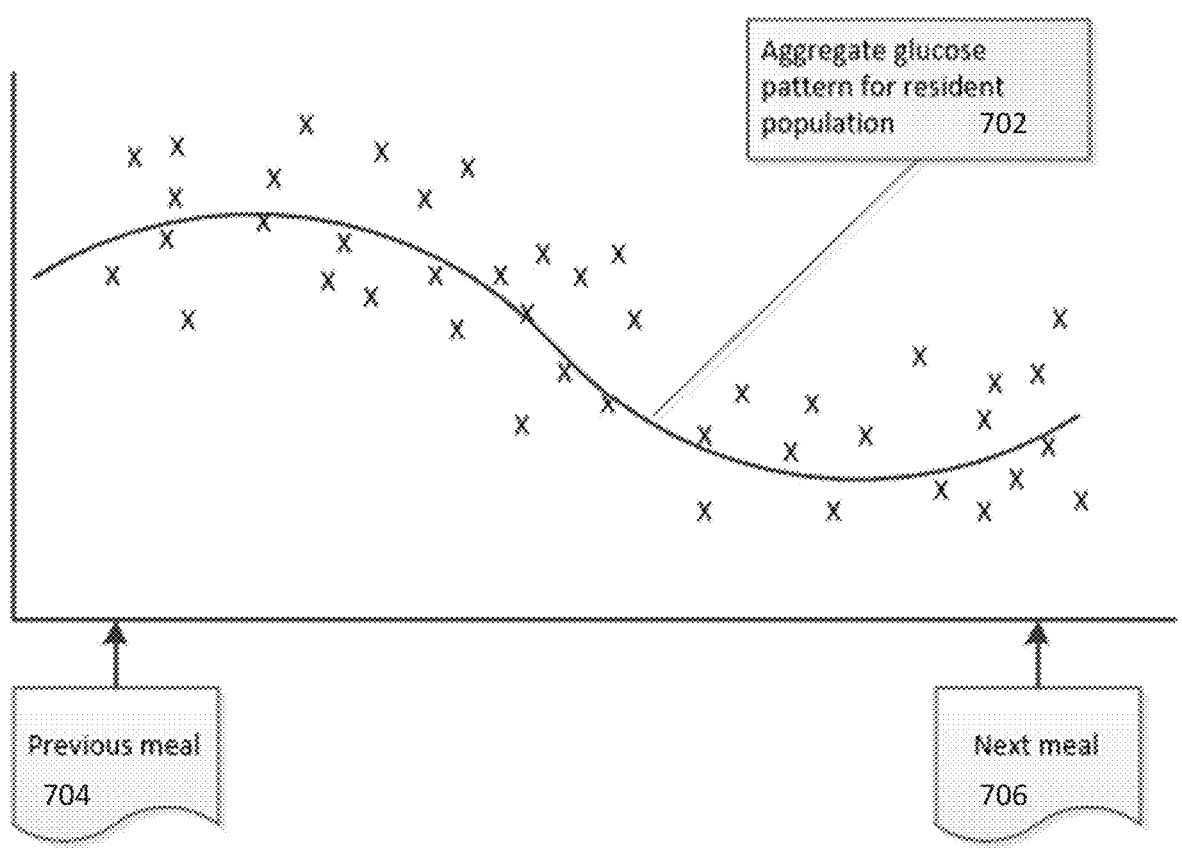
FIG. 7 depicts example aggregated analyte data for one or more (or all) individuals in a local population.

Trusted computer system 180 can be programmed to present the aggregate data to the user in graphical form such as that depicted in FIG. 7 or in the form of a summary report or the like. Trusted computer system 180 can also be programmed to determine or present analyte metrics for each individual wearer and statistics for the population as a whole (e.g., analyte median or mean, standard deviation, or average maximum or minimum values). FIG. 7 depicts a trend line 702 representative of the team analyte concentration for the resident population during a portion of a day with indicators for a first meal 704 and a subsequent meal 706.

Trusted computer system 180 can indicate trends for the resident population and identify instances where a portion of the population (e.g., 5%, 10%, 20%, etc.) violates a threshold or where the population trends in an undesirable manner. The threshold can be, for example, a low analyte threshold, a high analyte threshold, a rate of change threshold, or the like. The population may trend in an undesirable manner, for example, by the occurrence of a mean, median, or minimum-to-maximum variability that is undesirably high or low even if an excessive number of glucose excursions are not occurring. Trusted computer system 180 can be further programmed to provide a potential cause for the trend by reference to the meal information (e.g., excessive carbohydrate content, excessive sugar content, the occurrence of meals too frequently or not frequently enough, etc.) and also a recommendation as to how a meal aspect can be modified to relieve the trend. These recommendations can include adjustment of meal contents, adjustment of meal times, the introduction of a snack, the elimination of a snack, and adjustments to insulin dose amounts and times of administration (e.g., basal and bolus doses).

Trusted computer system 180 can also determine the analyte (e.g., glycemic) response or impact of each meal and provide a report that identifies meals that are associated with the most desirable or undesirable analyte traits. This information can be used by, e.g., a facility manager to alter the meal plans to maintain improved analyte levels across the population. For example, trusted computer system 180 can determine and store the glycemic response for each meal and output a ranking to assist in identifying the meals that cause the most severe responses. Any of the metrics described herein can be used to quantify or otherwise indicate the severity of the glycemic response, including, but not limited to peak glucose value, delta glucose value, and/or the glucose area.

A statistical analysis can be output, for example, glucose mean, glucose median, or glucose variability with standard deviations and/or interquartile ranges for each meal. The output can also include the results of a threshold comparison that, for example, outputs an indication of a mean or median of the population exceeding a threshold value, outputs a percent of the population with the means or medians exceeding a threshold value, outputs a variability for the population that exceeds a threshold value, and so forth.

In addition to those actions already mentioned, any number of actions can be taken for those members of the population identified as exceeding a threshold for a given meal, such as lowering the food portion, providing alternative food, or increasing insulin or other medication. Trusted computer system 180 can also identify individuals experiencing low glucose levels that may indicate too much insulin being administered for a particular meal.

Residences typically offer recreational activity and thus have the ability to select the type of activities and schedule these activities at the most effective times to reduce glucose rises. The embodiments described with respect to FIGS. 6A, 6B, and 7 can be used in conjunction with other activities that the population experiences, such as exercise.

For example, information about exercise events for the population can also be linked to the aggregated data in order to allow trusted computer system 180 to present the linked data and/or determine if correlations exist between analyte trends and the time, duration, and/or intensity of exercise events, in much the same manner as described above for meals. Each sensor control device 102 can include or otherwise be configured to operate with an activity monitor that continually measures the level of activity for each wearer (e.g., calories burned per time of day). Example embodiments of analyte monitoring systems that include or operate with activity monitors are described in the U.S. Provisional Patent Application titled "System, Device and Method of Dynamic Glucose Profile Response to Physiological Parameters," filed on the same date as the present application, and attached hereto as appendix A. The embodiments described in appendix A can each be used with any and all embodiments described herein for any and all purposes.

Embodiments of In Vivo Analyte Sensors

Analytes that may be monitored with system 100 include, but are not limited to, acetyl choline, amylase, bilirubin, cholesterol, chorionic gonadotropin, glycosylated hemoglobin (HbA1c), creatine kinase (e.g., CK-MB), creatine, creatinine, DNA, fructosamine, glucose, glucose derivatives, glutamine, growth hormones, hormones, ketones, ketone bodies, lactate, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be monitored. In embodiments that monitor more than one analyte, the analytes may be monitored at the same or different times.

Analyte sensor 104 may include an analyte-responsive enzyme to provide a sensing element. Some analytes, such as oxygen, can be directly electrooxidized or electroreduced on sensor 104, and more specifically at least on a working electrode (not shown) of a sensor 104. Other analytes, such as glucose and lactate, require the presence of at least one electron transfer agent and/or at least one catalyst to facilitate the electrooxidation or electroreduction of the analyte. Catalysts may also be used for those analytes, such as oxygen, that can be directly electrooxidized or electroreduced on the working electrode. For these analytes, each working electrode includes a sensing element proximate to or on a surface of a working electrode. In many embodiments, a sensing element is formed near or on only a small portion of at least a working electrode.

Each sensing element includes one or more components constructed to facilitate the electrochemical oxidation or reduction of the analyte. The sensing element may include, for example, a catalyst to catalyze a reaction of the analyte and produce a response at the working electrode, an electron transfer agent to transfer electrons between the analyte and the working electrode (or other component), or both.

A variety of different sensing element configurations may be used. In certain embodiments, the sensing elements are deposited on the conductive material of a working electrode. The sensing elements may extend beyond the conductive material of the working electrode. In some cases, the sensing elements may also extend over other electrodes, e.g., over the counter electrode and/or reference electrode (or counter/reference where provided). In other embodiments, the sensing elements are contained on the working electrode, such that the sensing elements do not extend beyond the conductive material of the working electrode. In some embodiments a working electrode is configured to include a plurality of spatially distinct sensing elements. Additional information related to the use of spatially distinct sensing elements can be found in US Publication No. 2012/0150005, entitled "Analyte Sensors with a Sensing Surface Having Small Sensing Spots," which was filed on Dec. 8, 2011, and which is incorporated by reference herein in its entirety and for all purposes.

The terms "working electrode", "counter electrode", "reference electrode" and "counter/reference electrode" are used herein to refer to conductive sensor components, including, e.g., conductive traces, which are configured to function as a working electrode, counter electrode, reference electrode or a counter/reference electrode respectively. For example, a working electrode includes that portion of a conductive material, e.g., a conductive trace, which functions as a working electrode as described herein, e.g., that portion of a conductive material which is exposed to an environment containing the analyte or analytes to be measured, and which, in some cases, has been modified with one or more sensing elements as described herein.

Similarly, a reference electrode includes that portion of a conductive material, e.g., conductive trace, which function as a reference electrode as described herein, e.g., that portion of a conductive material which is exposed to an environment containing the analyte or analytes to be measured, and which, in some cases, includes a secondary conductive layer, e.g., a Ag/AgCl layer. A counter electrode includes that portion of a conductive material, e.g., conductive trace which is configured to function as a counter electrode as described herein, e.g., that portion of a conductive trace which is exposed to an environment containing the analyte or analytes to be measured. As noted above, in some embodiments, a portion of a conductive material, e.g., conductive trace, may function as either or both of a counter electrode and a reference electrode. In addition, "working electrodes", "counter electrodes", "reference electrodes" and "counter/reference electrodes" may include portions, e.g., conductive traces, electrical contacts, or areas or portions thereof, which do not include sensing elements but which are used to electrically connect the electrodes to other electrical components.

Sensing elements that are in direct contact with the working electrode, e.g., the working electrode trace, may contain an electron transfer agent to transfer electrons directly or indirectly between the analyte and the working electrode, and/or a catalyst to facilitate a reaction of the analyte. For example, a glucose, lactate, or oxygen electrode may be formed having sensing elements which contain a catalyst, including glucose oxidase, glucose dehydrogenase, lactate oxidase, or laccase, respectively, and an electron transfer agent that facilitates the electrooxidation of the glucose, lactate, or oxygen, respectively.

In other embodiments the sensing elements are not deposited directly on the working electrode, e.g., the working electrode trace. Instead, the sensing elements may be spaced apart from the working electrode trace, and separated from the working electrode trace, e.g., by a separation layer. A separation layer may include one or more membranes or films or a physical distance. In addition to separating the working electrode trace from the sensing elements, the separation layer may also act as a mass transport limiting layer and/or an interferent eliminating layer and/or a biocompatible layer.

In certain embodiments which include more than one working electrode, one or more of the working electrodes may not have corresponding sensing elements, or may have sensing elements that do not contain one or more components (e.g., an electron transfer agent and/or catalyst) needed to electrolyze the analyte. Thus, the signal at this working electrode may correspond to background signal which may be removed from the analyte signal obtained from one or more other working electrodes that are associated with fully-functional sensing elements by, for example, subtracting the signal.

In certain embodiments, the sensing elements include one or more electron transfer agents. Electron transfer agents that may be employed are electroreducible and electrooxidizable ions or molecules having redox potentials that are a few hundred millivolts above or below the redox potential of the standard calomel electrode (SCE). The electron transfer agent may be organic, organometallic, or inorganic. Examples of organic redox species are quinones and species that in their oxidized state have quinoid structures, such as Nile blue and indophenol. Examples of organometallic redox species are metallocenes including ferrocene. Examples of inorganic redox species are hexacyanoferrate (III), ruthenium hexamine, etc. Additional examples include those described in U.S. Pat. Nos. 6,736,957, 7,501,053 and 7,754,093, the disclosures of each of which are incorporated herein by reference in their entirety.

In certain embodiments, electron transfer agents have structures or charges which prevent or substantially reduce the diffusional loss of the electron transfer agent during the period of time that the sample is being analyzed. For example, electron transfer agents include but are not limited to a redox species, e.g., bound to a polymer which can in turn be disposed on or near the working electrode. The bond between the redox species and the polymer may be covalent, coordinative, or ionic. Although any organic, organometallic or inorganic redox species may be bound to a polymer and used as an electron transfer agent, in certain embodiments the redox species is a transition metal compound or complex, e.g., osmium, ruthenium, iron, and cobalt compounds or complexes. Redox species described for use with a polymeric component may also be used without a polymeric component.

Embodiments of polymeric electron transfer agents may contain a redox species covalently bound in a polymeric composition. An example of this type of mediator is poly(vinylferrocene). Another type of electron transfer agent contains an ionically-bound redox species. This type of mediator may include a charged polymer coupled to an oppositely charged redox species. Examples of this type of mediator include a negatively charged polymer coupled to a positively charged redox species such as an osmium or ruthenium polypyridyl cation.

Another example of an ionically-bound mediator is a positively charged polymer including quaternized poly(4-vinyl pyridine) or poly(1-vinyl imidazole) coupled to a negatively charged redox species such as ferricyanide or ferrocyanide. In other embodiments, electron transfer agents include a redox species coordinatively bound to a polymer. For example, the mediator may be formed by coordination of an osmium or cobalt 2,2'-bipyridyl complex to poly(1-vinyl imidazole) or poly(4-vinyl pyridine).

Suitable electron transfer agents are osmium transition metal complexes with one or more ligands, each ligand having a nitrogen-containing heterocycle such as 2,2'-bipyridine, 1,10-phenanthroline, 1-methyl, 2-pyridyl biimidazole, or derivatives thereof. The electron transfer agents may also have one or more ligands covalently bound in a polymer, each ligand having at least one nitrogen-containing heterocycle, such as pyridine, imidazole, or derivatives thereof. One example of an electron transfer agent includes (a) a polymer or copolymer having pyridine or imidazole functional groups and (b) osmium cations complexed with two ligands, each ligand containing 2,2'-bipyridine, 1,10-phenanthroline, or derivatives thereof, the two ligands not necessarily being the same. Some derivatives of 2,2'-bipyridine for complexation with the osmium cation include but are not limited to 4,4'-dimethyl-2,2'-bipyridine and mono-, di-, and polyalkoxy-2,2'-bipyridines, including 4,4'-dimethoxy-2,2'-bipyridine. Derivatives of 1,10-phenanthroline for complexation with the osmium cation include but are not limited to 4,7-dimethyl-1,10-phenanthroline and mono, di-, and polyalkoxy-1,10-phenanthrolines, such as 4,7-dimethoxy-1,10-phenanthroline. Polymers for complexation with the osmium cation include but are not limited to polymers and copolymers of poly(1-vinyl imidazole) (referred to as "PVI") and poly(4-vinyl pyridine) (referred to as "PVP"). Suitable copolymer substituents of poly(1-vinyl imidazole) include acrylonitrile, acrylamide, and substituted or quaternized N-vinyl imidazole, e.g., electron transfer agents with osmium complexed to a polymer or copolymer of poly(1-vinyl imidazole).

Embodiments may employ electron transfer agents having a redox potential ranging from about −200 mV to about +200 mV versus the standard calomel electrode (SCE). The sensing elements may also include a catalyst which is capable of catalyzing a reaction of the analyte. The catalyst may also, in some embodiments, act as an electron transfer agent. One example of a suitable catalyst is an enzyme which catalyzes a reaction of the analyte. For example, a catalyst, including a glucose oxidase, glucose dehydrogenase (e.g., pyrroloquinoline quinone (PQQ), dependent glucose dehydrogenase, flavine adenine dinucleotide (FAD) dependent glucose dehydrogenase, or nicotinamide adenine dinucleotide (NAD) dependent glucose dehydrogenase), may be used when the analyte of interest is glucose. A lactate oxidase or lactate dehydrogenase may be used when the analyte of interest is lactate. Laccase may be used when the analyte of interest is oxygen or when oxygen is generated or consumed in response to a reaction of the analyte.

In certain embodiments, a catalyst may be attached to a polymer, cross linking the catalyst with another electron transfer agent, which, as described above, may be polymeric. A second catalyst may also be used in certain embodiments. This second catalyst may be used to catalyze a reaction of a product compound resulting from the catalyzed reaction of the analyte. The second catalyst may operate with an electron transfer agent to electrolyze the product compound to generate a signal at the working electrode. Alternatively, a second catalyst may be provided in an interferent-eliminating layer to catalyze reactions that remove interferents.

In certain embodiments, the sensor works at a low oxidizing potential, e.g., a potential of about +40 mV vs. Ag/AgCl. These sensing elements use, for example, an osmium (Os)-based mediator constructed for low potential operation. Accordingly, in certain embodiments the sensing elements are redox active components that include: (1) osmium-based mediator molecules that include (bidente) ligands, and (2) glucose oxidase enzyme molecules. These two constituents are combined together in the sensing elements of the sensor.

A mass transport limiting layer (not shown), e.g., an analyte flux modulating layer, may be included with the sensor to act as a diffusion-limiting barrier to reduce the rate of mass transport of the analyte, for example, glucose or lactate, into the region around the working electrodes. The mass transport limiting layers are useful in limiting the flux of an analyte to a working electrode in an electrochemical sensor so that the sensor is linearly responsive over a large range of analyte concentrations and is easily calibrated. Mass transport limiting layers may include polymers and may be biocompatible. A mass transport limiting layer may provide many functions, e.g., biocompatibility and/or interferent-eliminating functions, etc. A mass transport limiting layer may be applied to an analyte sensor as described herein via any of a variety of suitable methods, including, e.g., dip coating and slot die coating.

In certain embodiments, a mass transport limiting layer is a membrane composed of crosslinked polymers containing heterocyclic nitrogen groups, such as polymers of polyvinylpyridine and polyvinylimidazole. Embodiments also include membranes that are made of a polyurethane, or polyether urethane, or chemically related material, or membranes that are made of silicone, and the like.

A membrane may be formed by crosslinking in situ a polymer, modified with a zwitterionic moiety, a non-pyridine copolymer component, and optionally another moiety that is either hydrophilic or hydrophobic, and/or has other desirable properties, in an alcohol-buffer solution. The modified polymer may be made from a precursor polymer containing heterocyclic nitrogen groups. For example, a precursor polymer may be polyvinylpyridine or polyvinylimidazole. Optionally, hydrophilic or hydrophobic modifiers may be used to "fine-tune" the permeability of the resulting membrane to an analyte of interest. Optional hydrophilic modifiers, such as poly (ethylene glycol), hydroxyl or polyhydroxyl modifiers, may be used to enhance the biocompatibility of the polymer or the resulting membrane.

A membrane may be formed in situ by applying an alcohol-buffer solution of a crosslinker and a modified polymer over the enzyme-containing sensing elements and allowing the solution to cure for about one to two days or other appropriate time period. The crosslinker-polymer solution may be applied over the sensing elements by placing a droplet or droplets of the membrane solution on the sensor, by dipping the sensor into the membrane solution, by spraying the membrane solution on the sensor, and the like. Generally, the thickness of the membrane is controlled by the concentration of the membrane solution, by the number of droplets of the membrane solution applied, by the number of times the sensor is dipped in the membrane solution, by the volume of membrane solution sprayed on the sensor, or by any combination of these factors. In order to coat the distal and side edges of the sensor, the membrane material may have to be applied subsequent to singulation of the sensor precursors. In some embodiments, the analyte sensor is dip-coated following singulation to apply one or more membranes. Alternatively, the analyte sensor could be slot-die coated wherein each side of the analyte sensor is coated separately. A membrane applied in the above manner may have any combination of the following functions: (1) mass transport limitation, i.e., reduction of the flux of analyte that can reach the sensing elements, (2) biocompatibility enhancement, or (3) interferent reduction.

In some embodiments, a membrane composition for use as a mass transport limiting layer may include one or more leveling agents, e.g., polydimethylsiloxane (PDMS). Additional information with respect to the use of leveling agents can be found, for example, in US Patent Application Publication No. US 2010/0081905, the disclosure of which is incorporated by reference herein in its entirety.

In some instances, the membrane may form one or more bonds with the sensing elements. The term "bonds" is intended to cover any type of an interaction between atoms or molecules that allows chemical compounds to form associations with each other, such as, but not limited to, covalent bonds, ionic bonds, dipole-dipole interactions, hydrogen bonds, London dispersion forces, and the like. For example, in situ polymerization of the membrane can form crosslinks between the polymers of the membrane and the polymers in the sensing elements. In certain embodiments, crosslinking of the membrane to the sensing element facilitates a reduction in the occurrence of delamination of the membrane from the sensor.

Example embodiments of the subject matter described herein include, but are not limited to, the following.

In certain example embodiments, a method of processing analyte data is provided using an in vivo analyte monitoring system that can include a sensor control device and a reader device, and the method can include: receiving, at the reader device, analyte data sensed from an individual by the sensor control device; processing the analyte data to detect, with the reader device, a meal event in the analyte data received from the sensor control device, wherein the reader device has an adjustable sensitivity for the detection of the meal event; associating, by the reader device, meal information with a range of analyte data received from the sensor control device, the range of analyte data reflecting an analyte response of the individual to the meal; and displaying, by the reader device, information about the analyte response.

Embodiments of the method can further include receiving, at the reader device, meal information from the individual. Embodiments of the method can further include determining, by the reader device or another computing device, whether the meal information received from the individual corresponds to the detected event. Embodiments of the method can further include, if the meal information received from the individual does not correspond to the detected event, then prompting the individual to enter meal information about the detected event.

Prompting the individual to enter meal information about the detected event can include prompting the individual to take the photograph of the meal with a camera application of the reader device. Prompting the individual to enter meal information can also include prompting the individual to select meal information from a list of meal information options, which can include information about meals previously consumed by the individual. Also, the meal information received from the individual can further include a textual description of the meal. In some embodiments, if the individual or another user selects a meal information option that is a previously consumed meal that resulted in an analyte excursion, then the method can include immediately outputting a notification, e.g., on the reader device, that prior consumption of the selected meal resulted in an analyte excursion.

Embodiments of the method can include automatically determining, by the reader device, whether a currently set sensitivity setting for detecting the meal event is either too sensitive or not sensitive enough for detecting the meal event. Embodiments of the method can include, if it is determined by the reader device that the currently set sensitivity setting is either too sensitive or not sensitive enough for detecting the meal event, then automatically adjusting, by the reader device, the currently set sensitivity setting.

Embodiments of the method can include detecting, with the reader device, a plurality of meal events in temporal proximity with each other; associating, by the reader device, the plurality of meal events together as one meal cluster; and displaying information, on the reader device, about an analyte response to the meal cluster. Embodiments of the method can include determining, by the reader device or another computing device, if each meal event of the plurality of meal events is within a predetermined time range of another meal event of the plurality of meal events prior to associating the plurality of meal events together as one meal cluster. Embodiments of the method can include displaying information, on the reader device, about the analyte response to the meal cluster includes displaying a peak analyte value for the meal cluster. Embodiments of the method can include determining the peak analyte value for the meal cluster by identifying the highest value in the received analyte data occurring at a time between a first meal event of the plurality of meal events to have occurred and the expiration of a predetermined time range after the last meal event of the plurality of meal events to have occurred.

In certain example embodiments, an in vivo analyte monitoring system (e.g., a system capable of in vivo analyte monitoring) is provided that can include a sensor control device comprising an in vivo analyte sensor and a reader device that can include: wireless communication circuitry adapted to wirelessly communicate with the sensor control device; graphical user interface circuitry comprising a display; processing circuitry communicatively coupled with the wireless communication circuitry; and non-transitory memory comprising instructions stored thereon that are executable by the processing circuitry, and the instructions, when executed, cause the processing circuitry to: process analyte data received from the sensor control device to detect a meal event in the analyte data, wherein the sensitivity for the detection of the meal event is adjustable by the processor; associate the meal information with a range of analyte data received from the sensor control device, the range of analyte data reflecting an analyte response of the individual to the meal; and display information about the analyte response with the reader device.

In certain example embodiments, the non-transitory memory can include instructions that, when executed, cause the processing circuitry to: read meal information received from the individual; determine whether the meal information received from the individual corresponds to the detected event; prompt the individual to enter meal information about the detected event if the meal information received from the individual does not correspond to the detected event; prompt the individual to take the photograph of the meal with a camera application of the reader device; prompt the individual to enter free text describing the meal; or prompt the individual to select meal information from a list of meal information options, where the list of meal information options can include information about meals previously consumed by the individual.

In certain example embodiments, the non-transitory memory can include instructions that, when executed, cause the processing circuitry to: determine if the individual selects a meal information option that is a previously consumed meal that resulted in an analyte excursion and, if the individual selects a meal information option that is a previously consumed meal that resulted in an analyte excursion, immediately cause a notification to be output to the individual that prior consumption of the selected meal resulted in an analyte excursion. The non-transitory memory can also include instructions that, when executed, cause the processing circuitry to automatically determine whether a currently set sensitivity setting for detection of the meal event is either too sensitive or not sensitive enough for detection of the meal event and, in some embodiments, if it is determined that the currently set sensitivity setting is either too sensitive or not sensitive enough for detection of the meal event, then automatically adjust the currently set sensitivity setting.

In certain example embodiments, a system for monitoring analyte levels of a population is provided that can include: a plurality of sensor control devices, each sensor control device can include an in vivo analyte sensor, where each sensor control device is wearable by a different member of the population and configured to monitor an analyte level of that member with the in vivo analyte sensor; a reader device that can include: wireless communication circuitry adapted to wirelessly communicate with the plurality of sensor control devices; processing circuitry communicatively coupled with the wireless communication circuitry; and non-transitory memory comprising instructions stored thereon that are executable by the processing circuitry, the instructions, when executed, causing the processing circuitry to: for each sensor control device of the plurality of sensor control devices, collect analyte data from that sensor control device, the analyte data being indicative of the analyte level of the wearer of that sensor control device; and transfer the collected analyte data from the plurality of sensor control devices to a trusted computer system. The system can include the trusted computer system including processing circuitry and a non-transitory memory that comprises instructions executable by the processing circuitry, the instructions, when executed, causing the processing circuitry to: store the collected analyte data received from the reader device; associate the collected analyte data with meal information about one or more meals provided to the population; and output information indicative of the analyte levels of the population in relation to the meal information.

In certain example embodiments, the non-transitory memory of the reader device can include instructions that, when executed, cause the processing circuitry of the reader device to: monitor for sensor control devices that are within communication range and, for each sensor control device within communication range, cause the transfer of analyte data from that sensor control device to the reader device; or cause the transfer of analyte data from each sensor control device to the reader device in sequential fashion. The non-transitory memory of the reader device can include instructions that, when executed, cause the processing circuitry to read an identifier transmitted from each sensor control device and collect analyte data from only those sensor control devices identified by the identifier as being part of the population to be monitored.

In certain example embodiments, the non-transitory memory of the trusted computer system comprises instructions that, when executed, cause the processing circuitry of the trusted computer system to: identify an undesirable trend in the collected analyte data; and output a potential cause for that trend by reference to the meal information. The non-transitory memory of the trusted computer system can also include instructions that, when executed, cause the processing circuitry of the trusted computer system to output a recommendation to relieve the undesirable trend. In some embodiments, the analyte is glucose and the non-transitory memory of the trusted computer system includes instructions that, when executed, cause the processing circuitry of the trusted computer system to identify a glycemic impact of each meal for which meal information is associated with the collected analyte data.

In certain example embodiments, a method for monitoring analyte levels of a population is provided that can include: for each member of the population, collecting analyte data indicative of an analyte level of that member with a sensor control device, comprising an in vivo analyte sensor, worn by that member; wirelessly communicating the collected analyte data from each sensor control device to a common reader device; and electronically transferring the collected analyte data from the common reader device to a trusted computer system.

Certain example embodiments of the method can include the collected analyte data being wirelessly communicated from each sensor control device to the reader device when each sensor control device is in communication range with the reader device, the reader device being located in a common area of a residence for the population. The reader device can be located in a dining room of a senior care facility and the population can include senior citizens resident in that senior care facility.

Certain example embodiments of the method can include reading, by the reader device, an identifier transmitted from each sensor control device; and collecting analyte data, by the reader device, from only those sensor control devices identified by the identifier as being part of the population to be monitored. The method can include: storing, by the trusted computer system, the collected analyte data received from the reader device; associating, by the trusted computer system, the collected analyte data with meal information about one or more meals provided to the population; and outputting, by the trusted computer system, information indicative of the analyte levels of the population in relation to the meal information.

Certain example embodiments of the method can include identifying, by the trusted computer system, an undesirable trend in the collected analyte data and outputting, by the trusted computer system, a potential cause for that trend by reference to the meal information. The method can further include outputting, by the trusted computer system, a recommendation to relieve the undesirable trend, and/or identifying, by the trusted computer system, a glycemic impact of each meal for which meal information is associated with the collected analyte data.

In certain example embodiments, a method is provided of associating the meal information with analyte data using an in vivo analyte monitoring system that can include a sensor control device and a reader device, where the method can include: receiving, at the reader device, analyte data sensed from an individual by the sensor control device; detecting, with the reader device, a meal event in the analyte data received from the sensor control device, where the reader device has an adjustable sensitivity for the detection of the meal event; associating, by the reader device, the meal information with a range of analyte data received from the sensor control device, the range of analyte data reflecting an analyte response of the individual to the meal; displaying, by the reader device, a prompt for the entry of additional meal information; associating, by the reader device, additional meal information entered in response to the prompt with the range of analyte data; and displaying, by the reader device, information about the analyte response.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

To the extent the embodiments disclosed herein include or operate in association with memory, storage, and/or computer readable media, then that memory, storage, and/or computer readable media are non-transitory. Accordingly, to the extent that memory, storage, and/or computer readable media are covered by one or more claims, then that memory, storage, and/or computer readable media is only non-transitory.

In many instances entities are described herein as being coupled to other entities. It should be understood that the terms "coupled" and "connected" (or any of their forms) are used interchangeably herein and, in both cases, are generic to the direct coupling of two entities (without any non-negligible (e.g., parasitic) intervening entities) and the indirect coupling of two entities (with one or more non-negligible intervening entities). Where entities are shown as being directly coupled together, or described as coupled together without description of any intervening entity, it should be understood that those entities can be indirectly coupled together as well unless the context clearly dictates otherwise.

The subject matter described herein and in the accompanying figures is done so with sufficient detail and clarity to permit the inclusion of claims, at any time, in means-plus-function format pursuant to 35 U.S.C. section 112, part (f). However, a claim is to be interpreted as invoking this means-plus-function format only if the phrase "means for" is explicitly recited in that claim.

As used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

While the embodiments are susceptible to various modifications and alternative forms, specific examples thereof have been shown in the drawings and are herein described in detail. These embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the scope of the claims by features, functions, steps, or elements that are not within that scope.

What is claimed is:

1. A method of processing analyte data using an in vivo analyte monitoring system comprising a sensor control device and a reader device, the method comprising:
    detecting a meal event with the reader device by processing the analyte data received from the sensor control device having an in vivo analyte sensor, wherein the reader device has an adjustable sensitivity for detecting the meal event;
    associating, by the reader device, meal information with a range of analyte data received from the sensor control device, the range of analyte data reflecting an analyte response of the individual to the meal;
    displaying, by the reader device, information about the analyte response;
    automatically determining, by the reader device, whether a sensitivity setting for detecting the meal event is either too sensitive or not sensitive enough for detecting the meal event; and
    if it is determined by the reader device that the sensitivity setting is either too sensitive or not sensitive enough for detecting the meal event, then automatically adjusting, by the reader device, the sensitivity setting.

2. The method of claim 1, further comprising receiving, at the reader device, meal information from the individual.

3. The method of claim 2, further comprising determining whether the meal information received from the individual corresponds to the detected event.

4. The method of claim 2, further comprising:
prompting the individual to enter meal information about the detected event when the meal information received from the individual does not correspond to the detected event.

5. The method of claim 4, wherein prompting the individual to enter meal information about the detected event comprises prompting the individual to take the photograph of the meal with a camera application of the reader device, wherein the reader device is a smart phone.

6. The method of claim 4, wherein the meal information received from the individual further comprises a textual description of the meal.

7. The method of claim 4, wherein prompting the individual to enter meal information comprises prompting the individual to select meal information from a list of meal information options.

8. The method of claim 7, wherein the list of meal information options includes information about meals previously consumed by the individual.

9. The method of claim 8, wherein a notification that prior consumption of the selected meal resulted in an analyte excursion is immediately outputted when the individual or another user selects a meal information option that is a previously consumed meal that resulted in an analyte excursion.

10. The method of claim 1, further comprising:
detecting, with the reader device, a plurality of meal events in temporal proximity with each other;
associating, by the reader device, the plurality of meal events together as one meal cluster; and
displaying information, on the reader device, about an analyte response to the meal cluster.

11. The method of claim 10, further comprising determining if each meal event of the plurality of meal events is within a predetermined time range of another meal event of the plurality of meal events prior to associating the plurality of meal events together as one meal cluster.

12. The method of claim 11, wherein displaying information, on the reader device, about the analyte response to the meal cluster includes displaying a peak analyte value for the meal cluster.

13. The method of claim 12, further comprising determining the peak analyte value for the meal cluster by identifying the highest value in the received analyte data occurring at a time between a first meal event of the plurality of meal events to have occurred and the expiration of a predetermined time range after the last meal event of the plurality of meal events to have occurred.

14. An in vivo analyte monitoring system, comprising:
a sensor control device comprising an in vivo analyte sensor; and
a reader device comprising:
wireless communication circuitry adapted to wirelessly communicate with the sensor control device having an in vivo analyte sensor;
graphical user interface circuitry comprising a display;
processing circuitry communicatively coupled with the wireless communication circuitry; and
non-transitory memory comprising instructions stored thereon that, when executed, cause the processing circuitry to:
detect a meal event in the analyte data by analysis of the analyte data received from the sensor control device, wherein the sensitivity for the detection of the meal event is adjustable by the processor;
associate meal information with a range of analyte data received from the sensor control device, wherein the range of analyte data reflects an analyte response of the individual to the meal;
display information about the analyte response with the reader device;
automatically determine whether a sensitivity setting for detecting the meal event is either too sensitive or not sensitive enough for detecting the meal event; and
if it is determined by the reader device that the sensitivity setting is either too sensitive or not sensitive enough for detecting the meal event, then adjust the sensitivity setting.

15. The system of claim 14, wherein the non-transitory memory comprises instructions that, when executed, cause the processing circuitry to read meal information received from the individual.

16. The system of claim 15, wherein the non-transitory memory comprises instructions that, when executed, cause the processing circuitry to determine whether the meal information received from the individual corresponds to the detected event.

17. The system of claim 15, wherein the non-transitory memory comprises instructions that, when executed, cause the processing circuitry to prompt the individual to enter meal information about the detected event if the meal information received from the individual does not correspond to the detected event.

18. The method of claim 1, wherein automatically determining whether a sensitivity setting for detecting the meal event is either too sensitive or not sensitive enough for detecting the meal event comprises comparing a total number of meal events with a baseline number of meal events in a day.

19. The method of claim 1, wherein the sensitivity setting is automatically adjusted with a scaling factor.

20. The method of claim 1, wherein the sensitivity setting is automatically adjusted to a next set of predetermined sensitivity settings.

* * * * *